United States Patent
Schiller et al.

(10) Patent No.: US 9,649,444 B2
(45) Date of Patent: May 16, 2017

(54) POSITIVE DISPLACEMENT STOPPER FOR A PRE-FILLED SYRINGE

(71) Applicant: Becton, Dickinson and Company, Franklin Lakes, NJ (US)

(72) Inventors: Eric Schiller, Kinnelon, NJ (US); Michael Vincent Quinn, East Hanover, NJ (US); Johanna Torres, Oxnard, CA (US); E Guan, Parsippany, NJ (US); Anthony Economou, Sparta, NJ (US); Gang Ju, Fair Lawn, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1015 days.

(21) Appl. No.: 13/889,539

(22) Filed: May 8, 2013

(65) Prior Publication Data
US 2013/0253436 A1    Sep. 26, 2013

Related U.S. Application Data

(62) Division of application No. 12/133,041, filed on Jun. 4, 2008, now Pat. No. 8,475,415.

(60) Provisional application No. 60/941,851, filed on Jun. 4, 2007, provisional application No. 60/950,741, filed on Jul. 19, 2007.

(51) Int. Cl.
*A61M 5/315* (2006.01)

(52) U.S. Cl.
CPC .... *A61M 5/31513* (2013.01); *A61M 5/31511* (2013.01); *A61M 5/31515* (2013.01); *A61M 2005/31521* (2013.01); *A61M 2005/31523* (2013.01)

(58) Field of Classification Search
CPC .......... A61M 5/31511; A61M 5/31513; A61M 5/31515; A61M 2005/31516; A61M 2005/31521; A61M 2005/31523
USPC ........ 604/218, 219, 220, 222, 226, 228, 229
See application file for complete search history.

(56) References Cited

U.S. PATENT DOCUMENTS

| | | |
|---|---|---|
| 2,895,773 A | 7/1959 | McConnaughey |
| 3,176,595 A | 4/1965 | Schwartz |
| 3,809,082 A | 5/1974 | Hurschman |
| 3,939,833 A | 2/1976 | Hansson et al. |
| 4,215,701 A | 8/1980 | Raitto |
| 4,266,557 A | 5/1981 | Merry |
| 4,354,507 A | 10/1982 | Raitto |
| 4,363,329 A | 12/1982 | Raitto |

(Continued)

FOREIGN PATENT DOCUMENTS

| | | |
|---|---|---|
| CN | 1498661 A | 5/2004 |
| CN | 1795020 A | 6/2006 |

(Continued)

*Primary Examiner* — Bhisma Mehta
*Assistant Examiner* — Larry R Wilson
(74) *Attorney, Agent, or Firm* — The Webb Law Firm

(57) ABSTRACT

A stopper adapted for attachment with a plunger rod for use within a syringe barrel is disclosed. The stopper includes a main body defining an open rearward end and a closed front end. The open rearward end is adapted to receive a front forward end attachment portion of the plunger rod. The stopper also includes a core member integrally formed with said main body adjacent the closed front end. The core member includes a nose portion having a profile adapted to create a positive seal with an outlet opening of such syringe barrel.

14 Claims, 31 Drawing Sheets

(56) References Cited

U.S. PATENT DOCUMENTS

| | | |
|---|---|---|
| 4,500,310 A | 2/1985 | Christinger |
| 4,543,093 A | 9/1985 | Christinger |
| 4,687,467 A | 8/1987 | Cygielski |
| 4,931,043 A | 6/1990 | Ray et al. |
| 4,973,308 A | 11/1990 | Borras et al. |
| 4,986,820 A | 1/1991 | Fischer |
| 5,195,975 A | 3/1993 | Castagna |
| 5,201,709 A | 4/1993 | Capra et al. |
| 5,246,423 A | 9/1993 | Farkas |
| 5,314,416 A | 5/1994 | Lewis et al. |
| 5,395,345 A | 3/1995 | Gross |
| 5,397,313 A | 3/1995 | Gross |
| 5,411,488 A | 5/1995 | Pagay et al. |
| 5,411,489 A | 5/1995 | Pagay et al. |
| 5,496,285 A * | 3/1996 | Schumacher ...... A61M 5/31511 604/218 |
| 5,624,405 A | 4/1997 | Futagawa et al. |
| 5,688,252 A | 11/1997 | Matsuda et al. |
| 5,713,857 A | 2/1998 | Grimard et al. |
| 5,722,951 A | 3/1998 | Marano |
| 5,735,825 A | 4/1998 | Stevens et al. |
| 5,795,337 A | 8/1998 | Grimard |
| 5,899,881 A | 5/1999 | Grimard et al. |
| 6,017,330 A | 1/2000 | Hitchins et al. |
| 6,053,894 A | 4/2000 | Shadd, Jr. |
| 6,171,286 B1 | 1/2001 | Gross |
| 6,224,577 B1 | 5/2001 | Dedola et al. |
| 6,361,524 B1 | 3/2002 | Odell et al. |
| 6,511,459 B1 | 1/2003 | Fago |
| 6,575,938 B2 | 6/2003 | Sayama et al. |
| 6,743,216 B2 | 6/2004 | Odell et al. |
| 6,821,266 B2 | 11/2004 | Knepshield et al. |
| 6,872,191 B2 | 3/2005 | Lo |
| 6,991,618 B2 | 1/2006 | Lau et al. |
| 7,056,301 B2 | 6/2006 | Liu |
| 7,081,107 B2 | 7/2006 | Kito et al. |
| 7,111,848 B2 | 9/2006 | Tachikawa et al. |
| 7,534,233 B2 | 5/2009 | Schiller et al. |
| 7,798,377 B2 | 9/2010 | Imhof et al. |
| 8,075,535 B2 | 12/2011 | Carrel et al. |
| 2002/0022806 A1 | 2/2002 | Witowski |
| 2004/0010235 A1 | 1/2004 | Weilbacher et al. |
| 2004/0127859 A1 | 7/2004 | Ward |
| 2005/0154353 A1 * | 7/2005 | Alheidt ............ A61M 5/31515 604/218 |
| 2007/0088270 A1 | 4/2007 | Cude |

FOREIGN PATENT DOCUMENTS

| | | |
|---|---|---|
| CN | 1874814 A | 12/2006 |
| DE | 2024117 | 9/1971 |
| EP | 0654280 A1 | 5/1995 |
| FR | 1500009 | 1/1968 |
| JP | 62292168 A | 12/1987 |
| JP | 2002505161 A | 2/2002 |
| JP | 2002-263187 A | 9/2002 |
| JP | 2004283466 | 10/2004 |
| WO | 2005002652 A2 | 1/2005 |
| WO | 2005/061030 A1 | 7/2005 |
| WO | 2005070485 A1 | 8/2005 |
| WO | 2006074171 A1 | 7/2006 |

* cited by examiner

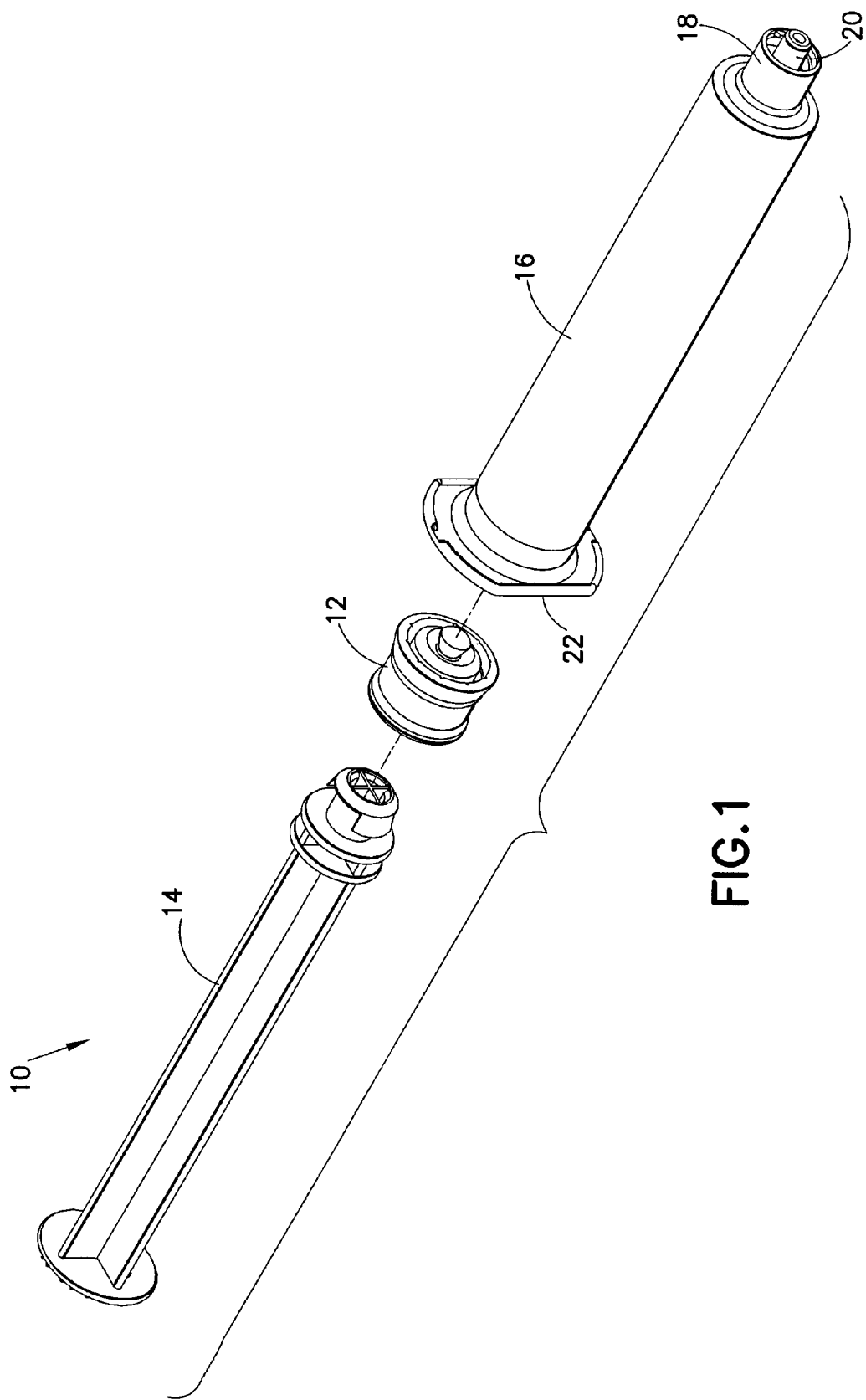

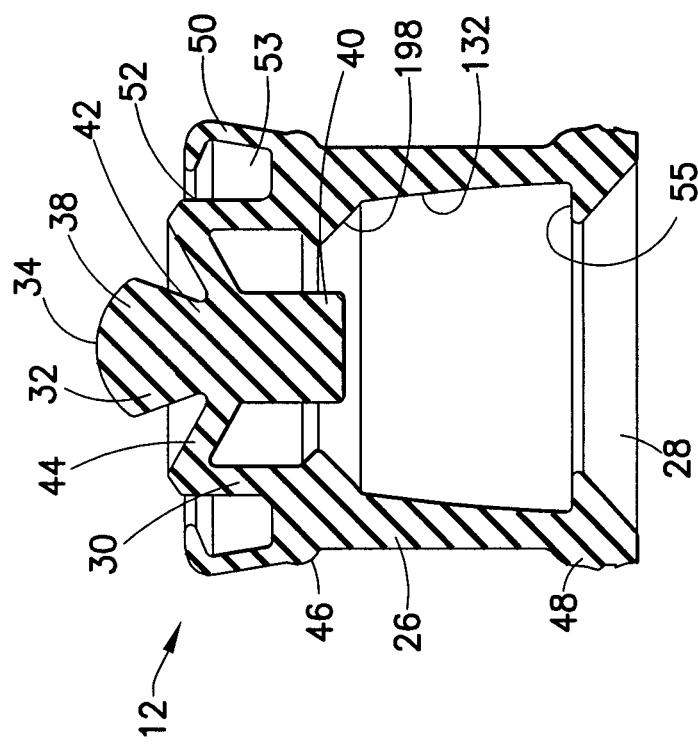
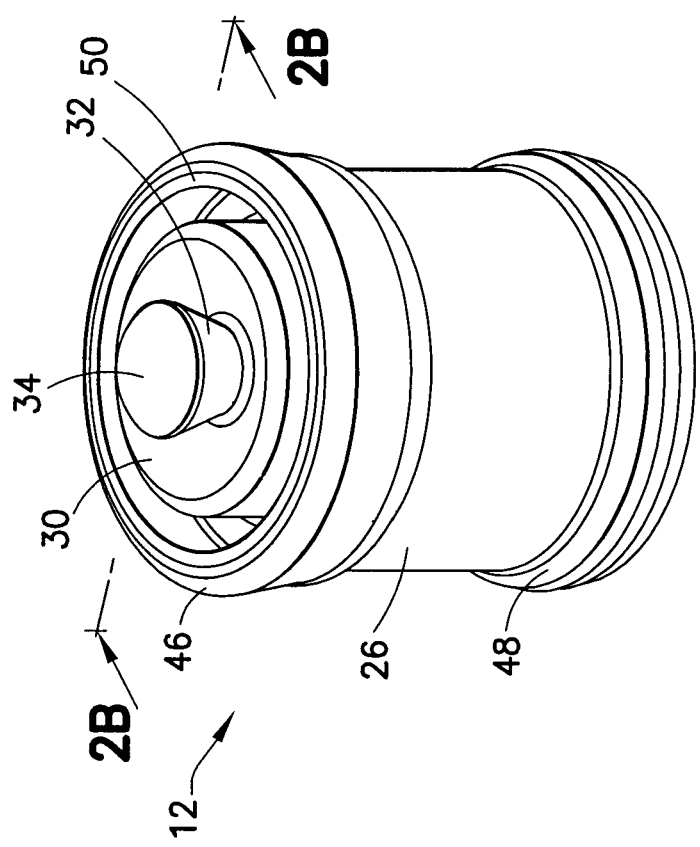
FIG.2B
FIG.2A

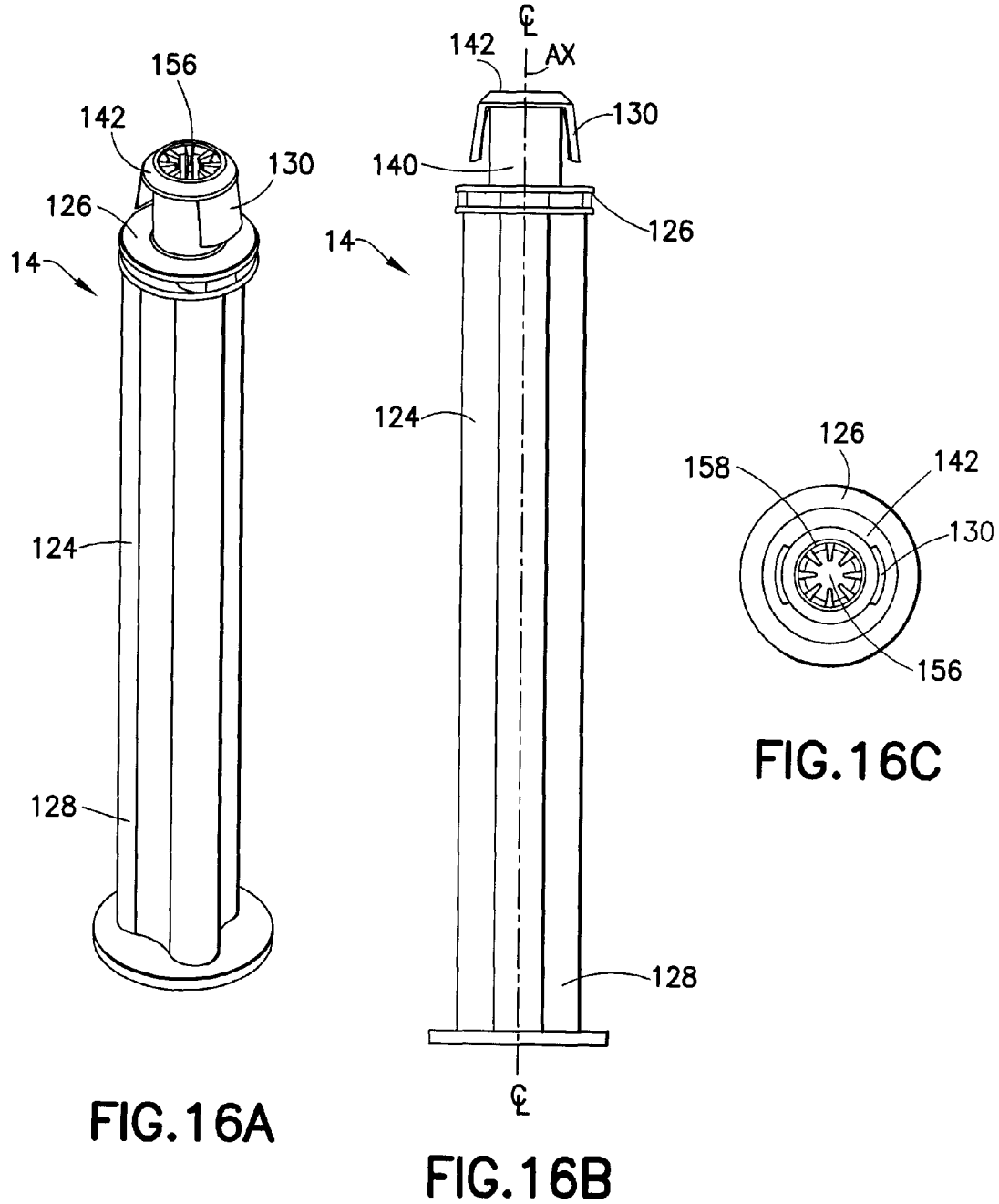

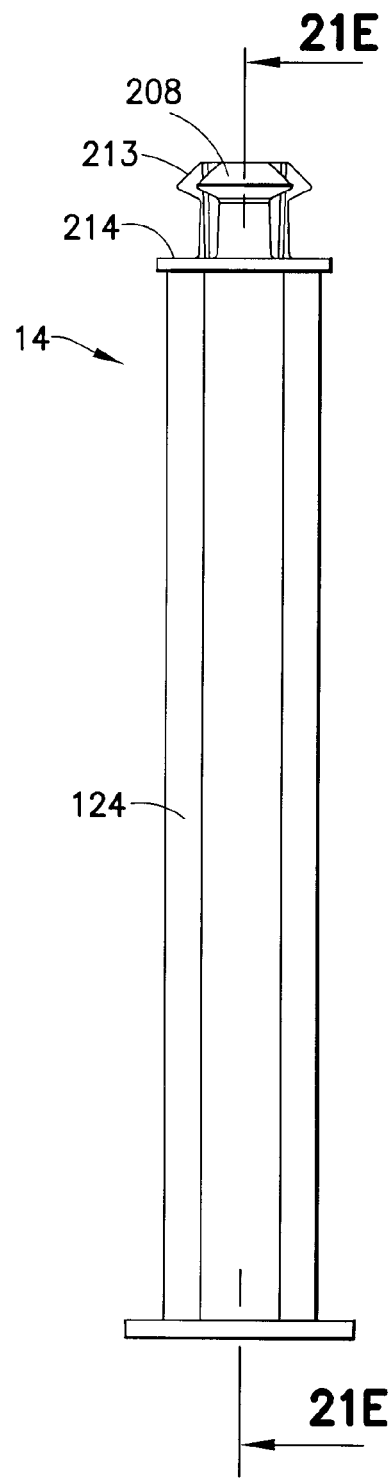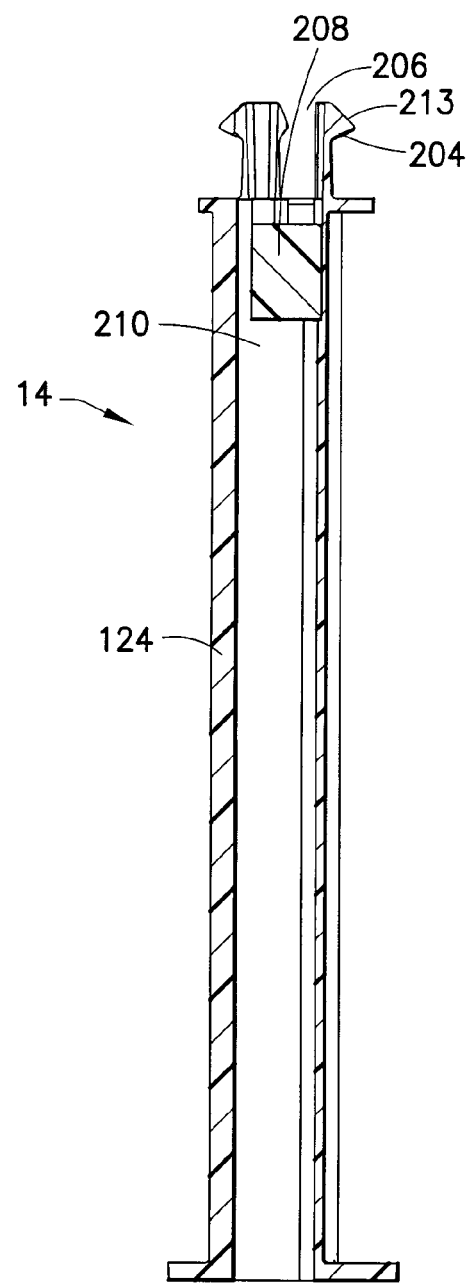
FIG.21C
FIG.21D

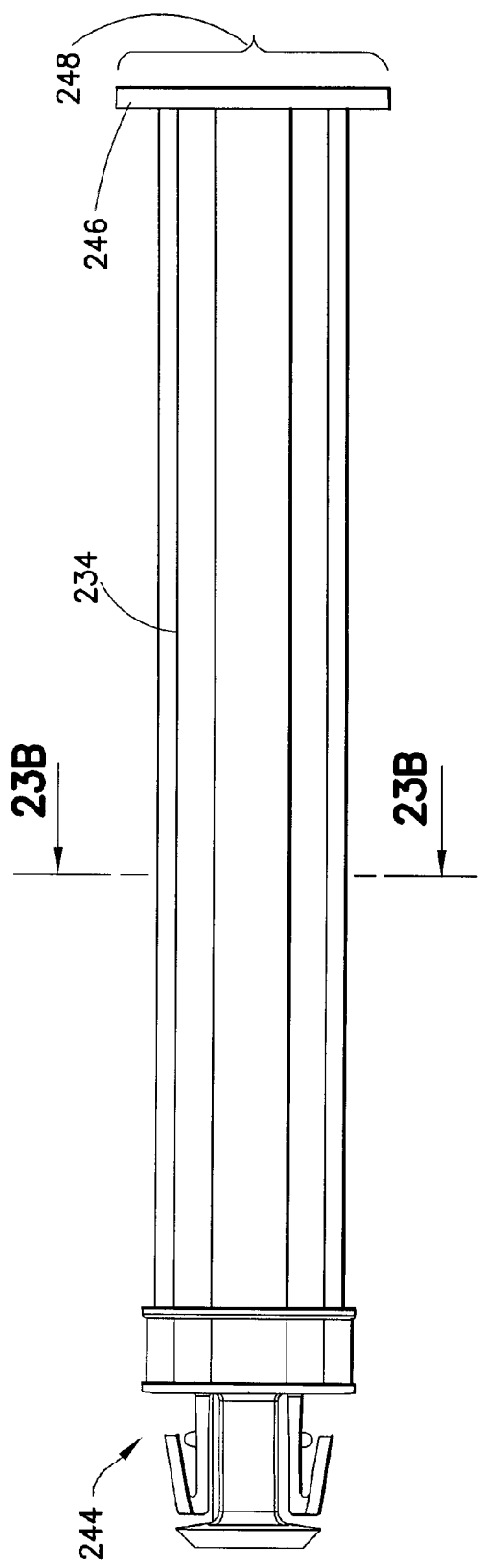
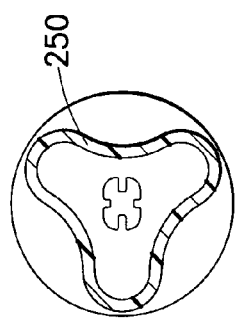
FIG.23A
FIG.23B

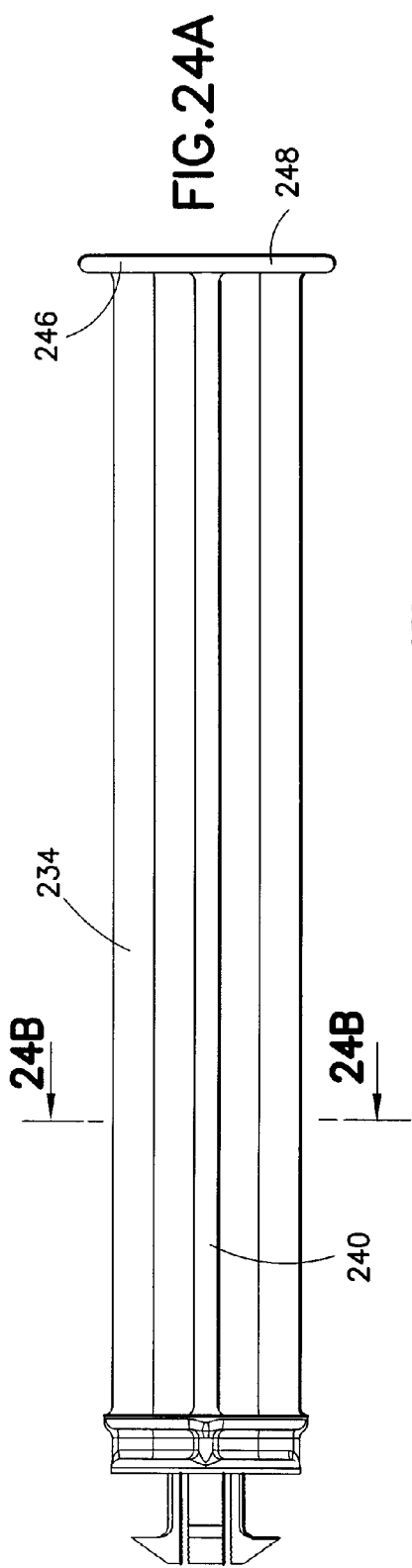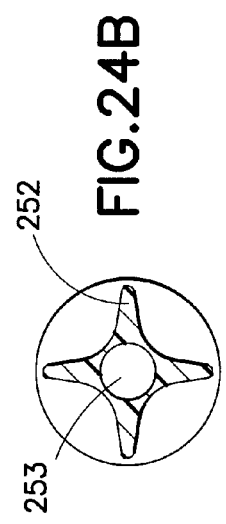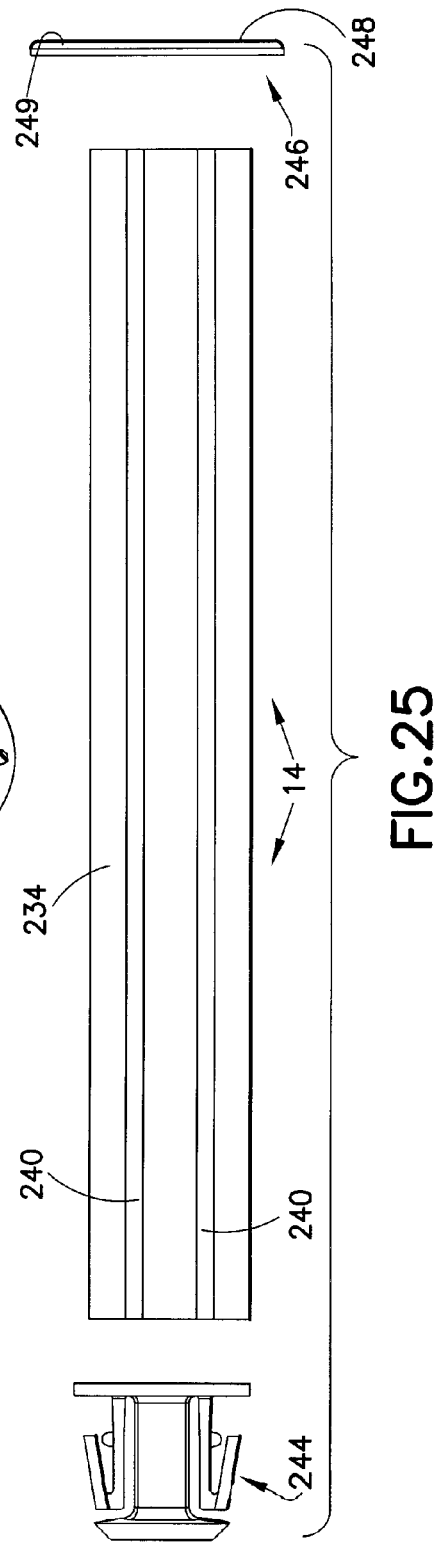

POSITIVE DISPLACEMENT STOPPER FOR A PRE-FILLED SYRINGE

CROSS REFERENCE TO RELATED APPLICATIONS

This application is a divisional of and claims priority to U.S. patent application Ser. No. 12/133,041 filed Jun. 4, 2008, entitled "Positive Displacement Stopper for a Pre-Filled Syringe" which claims priority to U.S. Provisional Patent Application No. 60/941,851, filed Jun. 4, 2007, entitled "Stopper and Plunger Rod for a Pre-Filled Syringe" and to U.S. Provisional Patent Application No. 60/950,741, filed Jul. 19, 2007, entitled "Positive Displacement Stopper for a Pre-Filled Syringe", the entire disclosures of each of which are hereby incorporated by reference in their entirety.

BACKGROUND OF THE INVENTION

Field of the Invention

The invention relates in general to a stopper assembly for use with a syringe and, more particularly, to a stopper assembly having a positive displacement feature for use with a pre-filled syringe such as those used in flush applications. The invention also relates to a plunger rod and an attachment member adapted for attachment with a stopper assembly.

Description of Related Art

Pre-filled syringes, such as those used in flush applications, are typically filled with a saline solution and are used to flush catheters. Example pre-filled syringes are shown in U.S. Pat. Nos. 6,361,524 and 6,743,216, which are incorporated herein by reference and which are directed to syringe assemblies for flush applications. At the end of the flushing procedure, the nurse or technician bottoms out the stopper in the syringe barrel. The process of bottoming the stopper in the barrel can cause a phenomenon known as reflux. Reflux is the reversal of fluid flow up through the catheter, usually due to the spring back of the stopper at the end of a flush injection. This occurs because the stopper compresses to force out additional saline, and subsequently springs back to shape. This causes the syringe to pull saline back into the syringe. This reflux can also pull blood back into the catheter, clogging it. This phenomenon of reflux is detrimental to the maintenance of the catheter line. Accordingly, it is desirable to reduce or eliminate reflux within the syringe.

Existing stopper designs typically include a constant diameter seal and a constant stopper-to-barrel interference to create a seal that will prevent fluid housed inside the barrel from leaking past the front seal of the stopper. The contact pressure of the seal is determined by the interference in these designs, and has to be sufficiently high enough such that they will not leak under the highest possible fluid pressure inside the barrel. The disadvantage of this traditional design is that the higher contact pressures lead to higher static and dynamic frictional forces. Static friction is commonly referred to as break loose force. Additionally, these existing stoppers typically include tip designs that are not self-centering. Because the tips are not self-centering, they do not form a positive seal with the inside back of the luer taper when subjected to axial forces.

Existing stopper designs have attempted to prevent the flow of fluid from the catheter back into the syringe when the clinician does not use a recommended positive pressure flushing technique, and release the force from the plunger rod prior to clamping the catheter. As discussed above, blood entering back into the distal catheter lumen is known as reflux and this reflux can lead to clogged catheters. These previous designs focused on preventing spring-back of the stopper that would create a vacuum to draw fluid back into the syringe. These designs, while effective in reducing reflux, do not consistently prevent all reflux from occurring.

Pre-filled syringes are typically manufactured in an automated process. The process of manufacturing these pre-filled syringes includes the steps of molding the syringe barrel, attaching the cap, filling the barrel, inserting the stopper, sterilizing the filled syringe, then inserting the plunger rod. Because the filled syringes are typically sterilized in an autoclave, size of the syringe is an issue. For this reason, the syringe is typically sterilized prior to the insertion of the plunger rod. Commonly used plunger rods are those of a snap-fit design, attached to the stopper prior to inserting the stopper into the barrel, or a threaded design, attached to the stopper after the stopper has been inserted into the barrel. Plunger rods assembled into the stopper after the stopper has been inserted into the barrel require a significant amount of force to be applied thereto during insertion. Axial forces applied to the plunger rod can cause the rod to become dislodged from the stopper, be misaligned, and/or break. Additionally, currently used snap-fit and/or threaded plunger rods occasionally become dislodged from the stopper during use.

Traditional plunger rods are typically cylindrical members, which are formed from a molded material. These known rods may have a ridged surface wherein four ribs, positioned 90° degrees with respect to one another, form the ridged surface. In this current four ribbed design, a user may apply a side load during flushing or aspiration that may be normal to the edge of the rib, causing minimal side loading deflection, or normal to the region between the ribs (45° from a rib), causing maximum side loading deflection. Additionally, the solid design of the stopper rod adds unnecessary material costs to the rod and may undesirably flex in an axial direction during use.

SUMMARY OF THE INVENTION

There is a need in the art for a stopper design that is self-centering to insure a seal with the syringe outlet to allow for pressure generation to create a positive displacement. There is a further need in the art for a stopper design that creates an active seal via the interaction of the stopper and plunger rod to transmit a radial force with respect to the barrel. The concept of an active seal involves an increase in pressure inside the syringe barrel which will cause the forward seal of the stopper to have a higher contact pressure with the inside walls of the barrel, maintaining a higher contact pressure than the internal fluid pressure, thereby preventing leakage at the stopper seal. There is yet another need in the art for a stopper design that includes a feature that allows for the capture and storage of potential energy prior to the release of the force from the plunger rod, effectively and consistently reducing and/or eliminating reflux of fluid back into the syringe upon this release of pressure on the plunger rod. There is also a need in the art for a plunger rod attachment design that can be easily inserted into the stopper of a pre-filled, sterilized syringe with the application of minimal force thereto and which is securely held within the stopper during use of the syringe. There is a further need in the art for a plunger rod design that uses a reduced amount of processing material, has a reduced molding cycle time, and has a high resistance to side loading.

The particularly disclosed stopper designs create a positive displacement of fluid out of the syringe (and therefore into any attached catheter, for example) after the stopper has been bottomed in the syringe barrel and force is released from the plunger rod so as to effectively and consistently reduce and/or eliminate reflux of fluid back into the syringe upon the release of pressure on the plunger rod. The stopper is adapted for attachment with a plunger rod for use within a syringe barrel.

According to one aspect of the invention, the stopper comprises a main body defining an open rearward end and closed front end. The open rearward end is adapted to receive a front forward end of the plunger rod. A core member is integrally formed with the main body adjacent the closed front end. The core member includes a nose portion having a profile adapted to create a positive seal with an interior surface of an outlet opening of the syringe barrel, such as through direct contact with an internal luer taper surface. The core member includes a front portion, a back portion, and a central portion positioned between the front and back portion wherein the front portion extends beyond the front end of the main body. The core member is interconnected with the main body via a flexible membrane extending between the core member and main body. At least one rib is provided that extends radially outward around the perimeter of the main body. This rib is adapted for forming an active seal with the syringe barrel. Two ribs may be provided which extend around a perimeter of the main body and are axially spaced apart along the main body. A skirt may also be provided which extends circumferentially from a forward end of the main body. This skirt is adapted for creating a positive pressure chamber therein and is formed from a flexible material capable of deflecting radially inwardly toward the main body and positioned at a location with respect to the main body to substantially close off the positive pressure chamber. According to an alternate embodiment, the main body includes at least one skirt extending therearound which is adapted for forming a lip seal with the syringe barrel. According to yet another alternate embodiment, the main body includes at least one radially extending shoulder extending from a front end of the main body. This shoulder is adapted for creating a positive pressure chamber. The stopper main body includes at least one undercut portion extending axially inward from the open rearward end. This undercut portion is adapted for locking the forward end of the plunger rod within the stopper. According to one design, the main body includes an inner surface having a taper adapted for contact with a corresponding taper on the forward end of the plunger rod such that the contacting tapers cooperate together and the stopper applies a radial force to a syringe barrel upon the application of a forward force to the plunger rod. According to an alternate design, the taper of the inner surface of the main body is a continuous contour from a side wall portion of the main body to the core member.

According to another aspect of the invention, the stopper, which is adapted for attachment with a plunger rod, includes a main body having a closed front end and a shoulder extending around a perimeter of the main body. A core member is integrally formed with the main body adjacent the closed front end. The core member includes a nose portion having a profile adapted to create a positive seal with an interior surface of an outlet of the syringe barrel. A perimetrical skirt is provided which extends toward the front end of the main body. The skirt cooperates with the shoulder for establishing a space between the main body and the skirt so as to create a positive fluid pressure therein upon insertion of the stopper within the syringe barrel. The stopper is particularly useful for positively displacing fluid out from within the syringe barrel. The main body includes an open rearward end which is adapted to receive a front portion of the plunger rod. The skirt is formed from a flexible material capable of deflecting radially inwardly toward and substantially in contact with the shoulder to establish the space. According to an alternate design, the skirt is adapted for deflecting radially inward and substantially into contact with a bottom portion of the shoulder. The main body includes a first body portion having a first diameter and a second body portion having a second diameter larger than the first diameter. The skirt extends from this second body portion about the first body portion. The shoulder extends radially outward from the first body portion for engagement with the skirt. The at least one skirt has a lip portion and a tail portion and an outer surface of the lip portion includes an outwardly extending perimetrical first rib adapted for contact with an inner surface of the syringe barrel. The tail portion of the skirt has an outer surface which is positioned a predetermined distance away from the inner surface of the syringe barrel to minimize the area of contact of the skirt with the syringe barrel to reduce break loose force and reduce static friction of the skirt with respect to the syringe barrel. The at least one skirt has a relatively cylindrical shape which extends concentrically about the first body portion of the main body. The core member includes a front portion, a back portion, and a central portion positioned between the front and back portion and this front portion extends beyond the front end of the main body. The core member is interconnected with the main body via a flexible membrane extending between the core member and the main body. The flexible membrane and the space between the skirt and the main body are adapted for storing potential energy such that upon release of a positive pressure on the plunger rod and release of the seal between the nose portion of the core member and the interior surface of the outlet, release of the potential energy forces fluid within the syringe through the outlet. The main body includes at least a second rib extending radially outward around a perimeter of the second body portion of the main body. The second rib is adapted for forming an active seal with the syringe barrel. The space between the skirt and the main body is positioned in a forward position with respect to the second rib. The main body can include at least a third rib and the second and third rib extend radially outward around a perimeter of the second body portion of the main body and axially spaced apart along this second body portion. The main body can further include at least one undercut portion extending axially inward the open rearward end. This undercut portion is adapted for locking the front portion of the plunger rod within the stopper. The undercut portion can include a reverse taper adapted for cooperation with the front portion of the plunger rod. Additionally, the main body can include an inner surface having a taper adapted for contact with a taper on the front attachment portion of the plunger rod. The contacting tapers cooperate together such that the stopper applies a radial force to the syringe barrel upon the application of a forward force to the plunger rod. In one embodiment of the invention, this taper of the inner surface of the main body is a continuous contour from a side wall portion of the main body to the core member.

According to yet another aspect of the invention, a stopper is provided which is adapted for attachment with a plunger rod for use within a syringe barrel for positively displacing fluid out from within such syringe barrel. The stopper comprises a main body having a closed front end and a shoulder extending around a perimeter of the main body. The main body includes an inner surface having a taper adapted for contact with a corresponding taper on a forward end of the plunger rod. The contacting tapers cooperate together such that the stopper applies a radial force to the syringe barrel upon the application of a forward force to the plunger rod. A core member is integrally formed with the main body adjacent the closed front end. The core member includes a nose portion wherein this nose portion has a profile adapted to create a positive seal with an interior surface of an outlet of the syringe barrel and wherein the inner surface of the main body is a continuous contour from a side wall portion of the main body to the core member. The stopper further includes a perimetrical skirt extending toward the front end of the main body. The skirt cooperates with the shoulder for establishing a space between the main body and the skirt so as to create a positive fluid pressure chamber.

According to another aspect of the invention, a positive displacement stopper is provided for attachment with a plunger rod for use within a syringe barrel of a flush syringe. The stopper includes a main body having a closed front end and a first body portion having a first diameter, a shoulder extending around a perimeter of the first body portion of the main body, a core member integrally formed with the main body adjacent the closed front end. The core member includes a nose portion which is adapted for contacting an interior surface of an outlet opening of the syringe barrel. The stopper also includes a perimetrical skirt extending toward the front end of the main body for cooperating with the shoulder for trapping air pockets therein upon insertion of the stopper within the syringe barrel such that upon release of a force on the plunger rod, fluid remaining within the syringe barrel is forced through the outlet opening through positive displacement thereof.

A method for positively displacing fluid and preventing reflux within a syringe barrel is also disclosed. This method includes providing a stopper comprising a main body having a closed front end, a first body portion having a first diameter, and a second body portion having a second diameter which is larger than the first diameter. A core member is integrally formed with the main body adjacent the closed front end. This core member includes a nose portion extending from the front end, a shoulder extending around the perimeter of the first portion of the main body, and a skirt extending about a perimeter of the first body portion at the front end of the main body. The skirt cooperates with the shoulder to trap at least one air pocket therein. The method further comprises advancing the stopper through the syringe barrel until the nose portion of the core member contacts an outlet opening at the forward end of the syringe, thereby forming a seal therewith and trapping fluid within the syringe from flowing out of the opening of the syringe. Additional force is applied to the stopper to compress the nose portion, thereby compressing the trapped air and increasing the pressure within the air pockets, and then releasing the force on the stopper to release the seal between the nose portion and the outlet opening at the forward end of the syringe while maintaining the main body of the stopper fixed within the syringe barrel, such that the increased pressure within the air pocket causes any trapped fluid to be expelled through the outlet opening. The main body of the stopper includes an open rearward end with a plunger rod inserted within the open rearward end. The nose portion of the stopper has a profile adapted to create a positive seal with the interior surface of the outlet opening of the syringe barrel. The core member is interconnected with the main body via a flexible membrane. The step of applying additional force to the stopper to compress the nose portion causes the flexible membrane to stretch and the step of releasing the force releases the flexible membrane to cause any trapped fluid to be expelled through the outlet opening. The stopper further includes a first rib on an outer surface of the skirt and at least a second rib extending radially outward around the second portion of the main body and wherein the step of applying additional force to the stopper advances the second rib within the syringe barrel and compresses the trapped air and increases the pressure within said air pockets. This second rib is maintained in an advanced position relative to the starting position within the syringe barrel when the force on the stopper is released, thereby maintaining the main body of the stopper fixed within the syringe barrel.

According to another aspect of the invention, a method of preventing reflux within a syringe barrel comprises providing a stopper having a main body defining an open rearward end and a closed front end. The open rearward end is adapted to receive a front attachment member of a plunger rod therein. A core member, having a nose portion, is integrally formed with the main body adjacent the closed front end. The method further includes inserting a front attachment member of a plunger rod within the open rearward end of the stopper and applying a force to the plunger rod to advance the stopper into the syringe barrel until the nose portion of the core member contacts an outlet opening at the front end of the syringe barrel forming a seal and trapping fluid from flowing out into the outlet opening. The method further includes applying additional force to the plunger rod to compress at least a portion of the stopper, so as to advance the at least one rib within the syringe barrel and to compress the trapped fluid to form increased pressure and subsequently releasing the force on the plunger rod to release the seal between the nose portion and the outlet opening of the syringe barrel wherein friction force maintains the rib in an advanced position within the syringe barrel such that the increased pressure causes any trapped fluid to be pushed through the outlet opening. The nose portion of the core member has a profile adapted to create a positive seal with an interior surface of the outlet opening of the syringe barrel. The core member is interconnected with the main body via a flexible membrane. The stopper further comprises at least one rib extending radially outward around a perimeter of the main body and at least one forward extending skirt extending from a front end of the main body. The step of applying a force to advance the stopper into the syringe barrel causes this skirt to deflect inward with respect to the stopper main body and to substantially contact the stopper main body, thereby trapping fluid within a space between said skirt and said main body. The main body can further include a shoulder extending around a perimeter of the main body such that the skirt extends inwardly and substantially contacts the shoulder, thereby establishing the space between the skirt and the main body. The step of applying additional force to the plunger rod to compress the nose portion causes the membrane to stretch and the step of releasing the force on the plunger rod releases this force on the flexible membrane to cause any trapped fluid to be pushed through the outlet opening.

According to another aspect of the invention, a plunger rod and stopper assembly adapted for use with a syringe barrel is provided. The assembly includes a plunger rod having a front attachment end and a back end and extending along a longitudinal axis and at least one deflecting arm associated with the attachment end of the elongated member.

The deflecting arm is adapted to deflect radially inward upon an application of force thereto and to deflect radially outward upon a release of such force. The assembly also includes a stopper having a main body defining an open rearward end, a closed front end, and a core member integrally formed with the main body adjacent the closed front end. The core member includes a nose portion having a profile adapted to create a positive seal with an outlet opening of the syringe barrel. The open rearward end is defined by an inside wall surface and an undercut portion and is adapted for receiving the front attachment end of the plunger rod such that the deflecting arm is deflected during insertion of the front attachment end and deflects outward after insertion to become trapped between at least a portion of the inside wall surface and the undercut portion to lock the plunger rod within the stopper.

According to yet another aspect of the invention, the stopper, adapted for attachment with a plunger rod for use within a syringe barrel, includes a main body defining an open rearward end and a closed front end. The open rearward end is adapted to receive a front forward end of the plunger rod. At least one rib extends radially outward around a perimeter of the main body. The stopper further includes at least one forward extending skirt extending from a front end of the main body. The at least one skirt is adapted for creating a positive pressure chamber therein.

According to still another aspect of the invention, a plunger rod and stopper assembly adapted for use with a syringe barrel is provided. The assembly includes a plunger rod having a front attachment end and a back end and extends along a longitudinal axis. The assembly further includes a stopper having a main body defining an open rearward end, a closed front end, and a core member integrally formed with the main body adjacent the closed front end. The open rearward end is defined by an inside wall surface and is adapted for receiving the front attachment end of the plunger rod and locking the plunger rod within the stopper wherein a gap is provided between a front surface of the front attachment end of the plunger and a back end of the core member. A flexible membrane extends between the core member and the main body for interconnecting the core member with the main body, wherein during application of a forward force to the plunger rod, the flexible membrane is adapted for causing the core member to retract with respect to the stopper main body and store potential energy such that upon a release of the forward force thereto, the potential energy is released causing the core member to advance with respect to the main body of the stopper and prevent midstream reflux within the syringe barrel.

BRIEF DESCRIPTION OF THE DRAWINGS

FIG. 1 is an exploded perspective view of a plunger rod, stopper, and syringe barrel in accordance with an embodiment of the present invention.

FIG. 2A is a perspective view of a stopper according to a first embodiment of the present invention.

FIG. 2B is a cross-sectional side view of the stopper of FIG. 2A take along line 2B-2B.

FIG. 16A is a perspective view of the plunger rod of FIG. 1.

FIG. 16B is a side view of the plunger rod of FIG. 1.

FIG. 16C is a top view of the plunger rod of FIG. 1.

FIG. 21C is a side view of the plunger rod of FIG. 21B.

FIG. 21D is a side view of the plunger rod of FIG. 21A wherein the reinforcing slug is positioned within a hollow portion of the plunger rod.

FIG. 23A is a side view of the plunger rod according to a second embodiment of the invention.

FIG. 23B is a cross-sectional view of the plunger rod of FIG. 23A taken along line 23B-23B.

FIG. 24A is a side view of the plunger rod according to a third embodiment of the invention.

FIG. 24B is a cross-sectional view of the plunger rod of FIG. 24A taken along line 24B-24B.

FIG. 25 is an exploded side view of the individual components of the plunger rod, which may be separately formed, in accordance with an embodiment of the present invention.

DETAILED DESCRIPTION OF THE INVENTION

Figure 3:
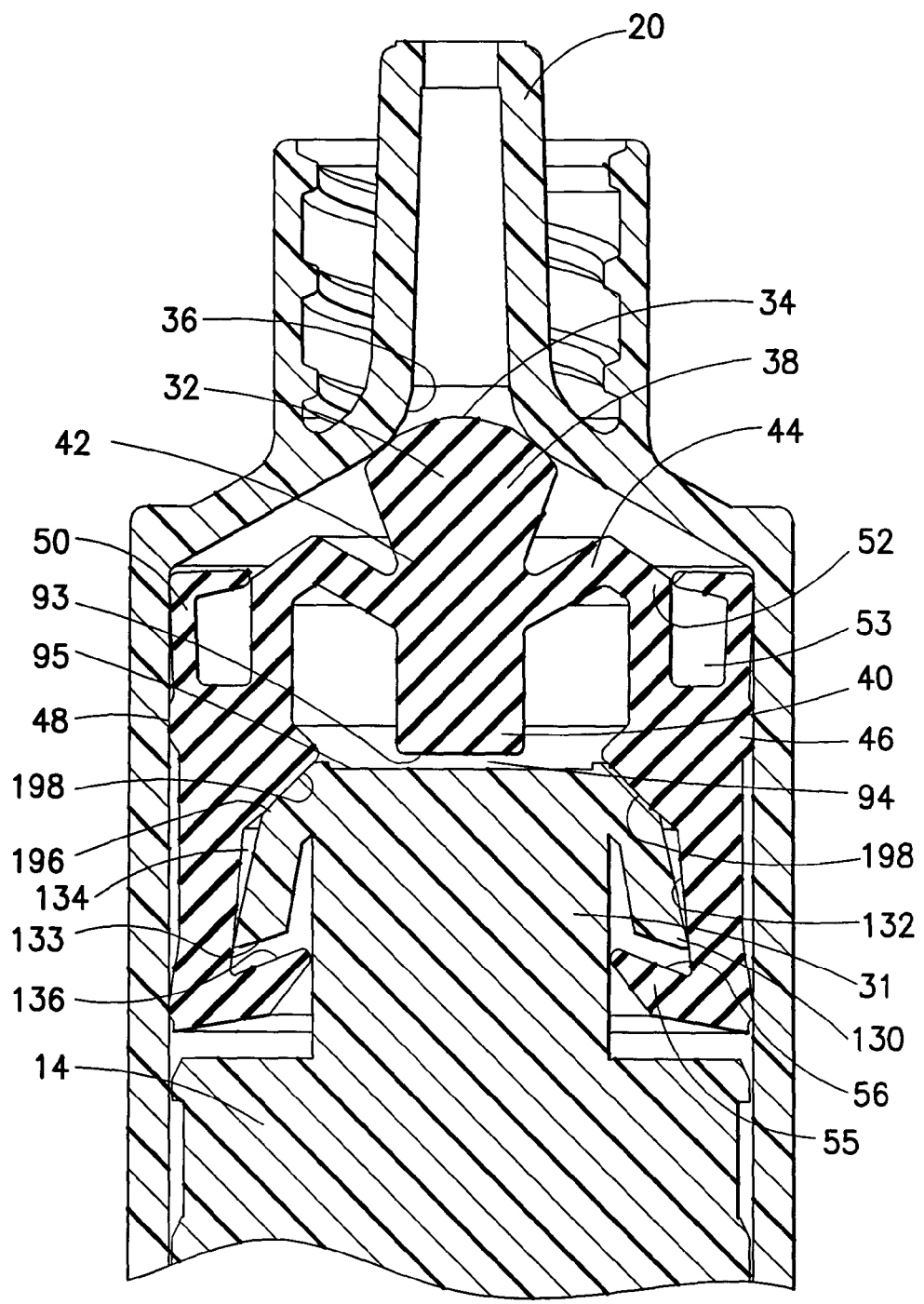
FIG. 3 is a cross-sectional side view of the stopper of FIG. 2A attached to a plunger rod and positioned within a syringe barrel.

For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is now made to FIG. 1, which shows a perspective view of a syringe, generally indicated as 10. The syringe comprises a stopper 12 and a plunger rod 14. The stopper 12 and plunger rod 14 are adapted for use within a syringe barrel 16. The syringe 10 is preferably of a type that is pre-filled and sterilized for use in flush applications. The syringe barrel 16 includes a distal or frontal end 18 which includes an outlet opening and/or a mechanism for attachment of a separate medical device (such as a catheter), shown in the form of a luer 20, and an open proximal or rearward end 22 for receiving the stopper 12 and plunger rod 14 assembly. While the figures herein depict a separate stopper and plunger assembly, it is contemplated that the stopper features may be integrally formed with a plunger rod 14.

Figure 4B:
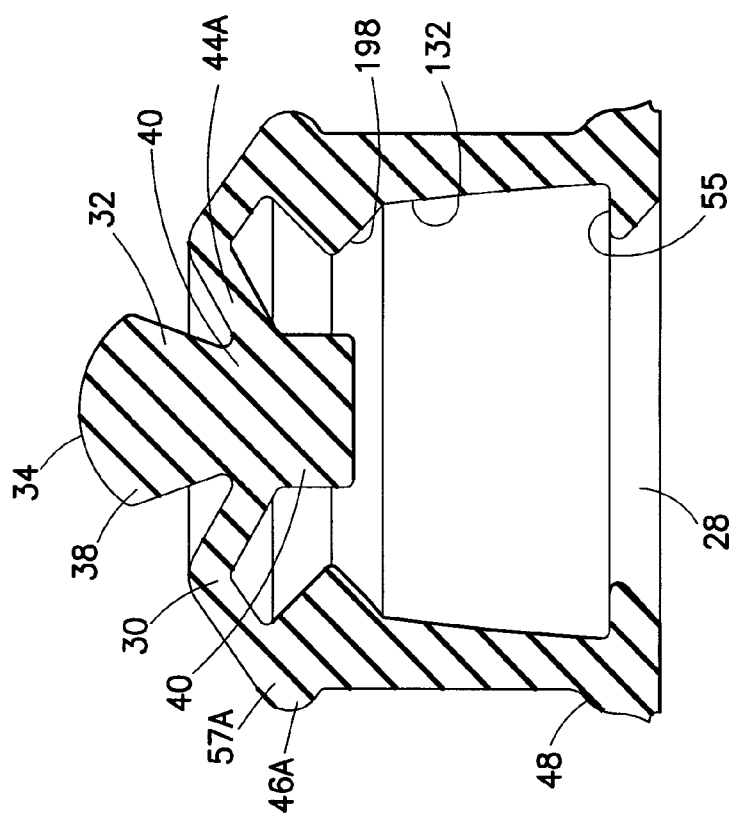
FIG. 4B is a cross-sectional side view of the stopper of FIG. 4A taken along line 4B-4B.
Figure 4A:
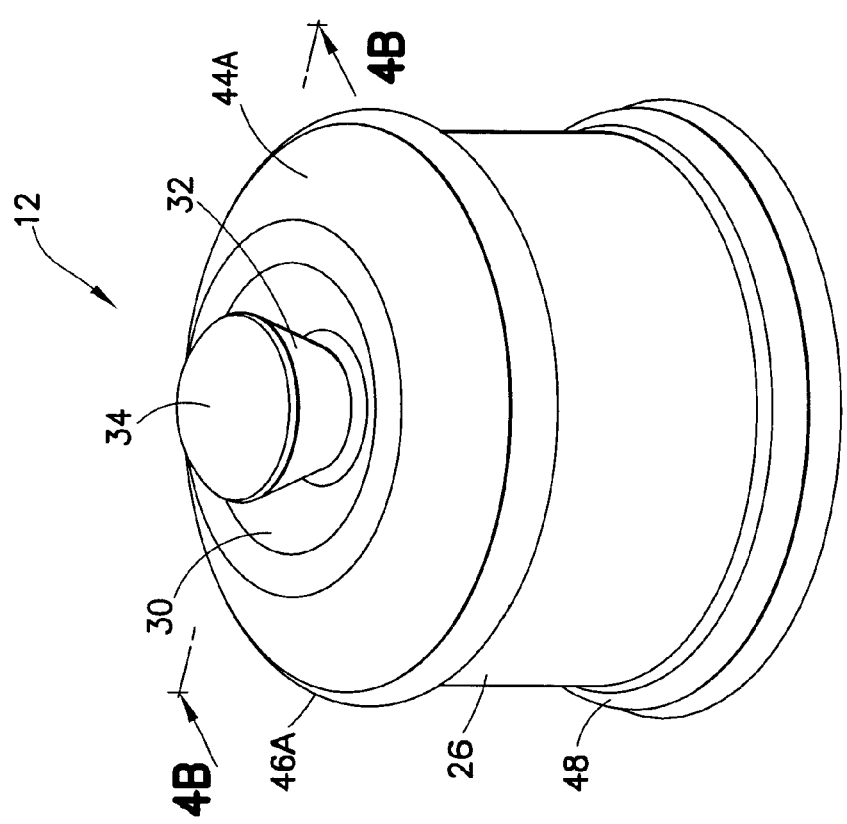
FIG. 4A is a perspective view of a stopper according to a second embodiment of the invention in accordance with an embodiment of the present invention.
Figure 6A:
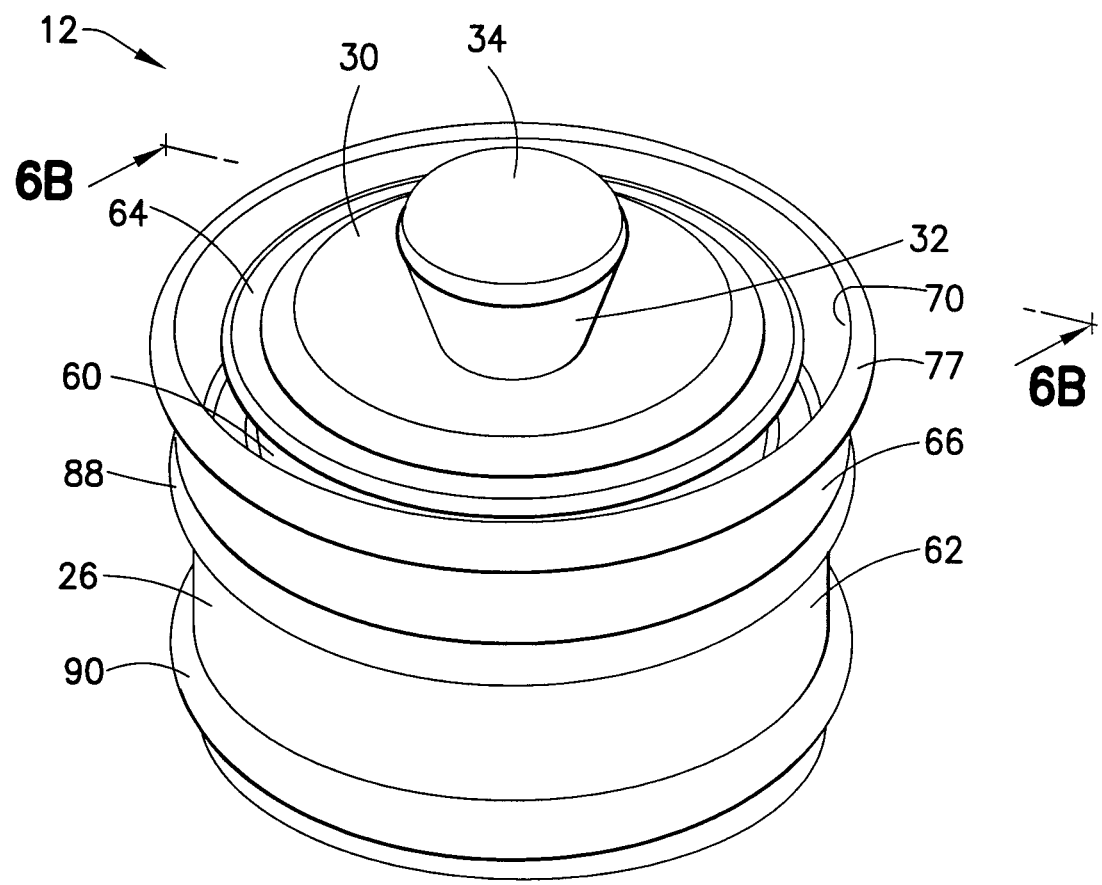
FIG. 6A is a perspective view of a stopper according to a fourth embodiment of the invention in accordance with an embodiment of the present invention.

Reference is now made to FIGS. 2A, 4A, and 6A which show perspective views of the positive displacement stopper 12 according to several different embodiments of the invention. FIGS. 2B, 4B, and 6B-6D show cross-sectional views of the different stopper embodiments in which the details of the positive displacement features of the stopper with respect to the syringe 10 can be readily viewed, wherein like elements are denoted by consistent numbering between the figures. The stopper 12 is adapted for attachment with a plunger rod 14 for use within a syringe barrel 16. The stopper 12 is preferably made of an elastomeric material selected from the group of natural rubber, synthetic rubber, thermoplastic elastomers, or combinations thereof. The stopper 12 of the invention is particularly useful with flush syringes such as those for use in connection with a catheter, as is well known in the art.

The stopper includes a main body 26 defining an open rearward end 28 and a closed front end 30. The open rearward end 28 is adapted to receive the front forward end attachment portion 31 of the plunger rod 14. The front forward end attachment portion 31 can be of any known design which is capable of attachment to the stopper 12; however, the present invention includes several inventive attachment members which are adapted for use with the stopper 12 of the present invention. These inventive attachment members are discussed in further detail below.

The stopper 12 further includes a flexible core member 32 integrally formed with the main body 26 adjacent the closed front end 30. As shown in FIG. 3, the flexible core member 32 includes a nose portion 34 having a profile adapted to be self-centering such that even when the stopper 12 is not centered in the syringe barrel 16, it creates a positive seal with an outlet opening of the syringe barrel 16, such as an interior surface 36 of a luer 20 of the syringe barrel 16. Once the stopper 12 has travelled the full distance through the syringe barrel 16 and contacts the internal surface at the forward wall or interior surface 36 of the syringe barrel 16 a positive seal may be formed therewith. In one embodiment, the nose portion 34 has a semi-spherical shape, which is self-centering such that even when the stopper 12 is not centered in the syringe barrel 16, it creates a positive seal with the outlet opening or luer 20 once the stopper 12 is bottomed in the syringe barrel 16. The nose portion 34 of the flexible core member 32 may include other shapes such as substantially conical, cubic, and/or any other volumetric shape capable of self-centering itself with respect to an outlet opening or luer 20 of the syringe barrel 16. This seal prevents excess fluid from being forced out of the syringe 10 once the stopper 12 is bottomed in the syringe barrel 16. Excess fluid expelled at the end of an injection can cause a phenomenon known as "reflux" when the stopper 12 springs back to shape and pulls that excess fluid back into the syringe 10. In the design of the present invention, the seal also allows the buildup of pressure within the fluid trapped between the stopper 12 and the syringe barrel 16, which in turn will lead to positive displacement of the fluid once pressure is released. This positive displacement of the fluid to prevent reflux is discussed in more detail below.

The flexible core member 32 includes a front portion 38, a back portion 40, and a central portion 42, positioned between the front portion 38 and back portion 40. The front portion 38 projects from the main body 26, such as along a longitudinal axis of the main body 26. The flexible core member 32 may be interconnected with the main body 26 via a flexible membrane 44 extending between the flexible core member 32 and the main body 26. The back portion 40 of this flexible core member 32 contacts the front forward end attachment portion 31 of the plunger rod 14. The inventive design of the self-centering nose portion 34 allows for a seal to be made when a small amount of force is applied to the stopper 12 and over the entire tolerance ranges of the stopper 12 and syringe barrel 16.

As discussed above, the sealing surface on the nose portion 34 comes into contact with the interior surface 36 or back surface of the conical luer 20 at the front end of the syringe barrel 16, shown in FIG. 1. Since it is possible that the interior surface 36 of the luer 20 and the nose portion 34 of the stopper 12 will not be perfectly concentric, in one embodiment, the nose portion 34 of the stopper 12 may be capable of moving laterally in order for it to make full contact with the interior surface 36 of the luer 20. In a further embodiment, the flexible core member 32 and the flexible membrane 44 may allow the nose portion 34 to move in a substantially lateral direction. In yet another embodiment, the partially spherical shape of the nose portion 34 assures full contact between the nose portion 34 and the interior surface 36 of the luer 20 even when the nose portion 34 has rotated or shifted prior to making contact.

The inventive design of the stopper 12 of the present invention is an improvement over current stoppers as these current stoppers typically have a conical tip and work to seal only when the stopper and barrel are perfectly concentric. In prior designs, if the two components are not exactly aligned, there will not be a proper seal unless higher forces are applied to the stopper in order to deform it into a shape that will seal with the barrel luer taper.

According to a first embodiment of the stopper 12, as illustrated in FIGS. 2A, 2B, and 3, and a second embodiment of the stopper 12, as illustrated in FIGS. 4A and 4B, the main body 26 includes at least a first rib 46 extending radially outward and substantially around a perimeter of the main body 26. This first rib 46 is adapted for forming an active seal with the syringe barrel 16. In one embodiment, the main body 26 includes a second rib 48 extending substantially around a perimeter of the main body 26. The first rib 46 and the second rib 48 may be axially spaced apart along the length of the main body 26.

A feature of the stopper design of the first embodiment illustrated in FIGS. 2A, 2B and 3 is a forward extending skirt 50 extending from the closed front end 30 of the main body 26. Due to the elasticity and/or flexibility of the forward extending skirt 50, the forward extending skirt 50 is capable of deforming by deflecting radially inwardly toward and substantially in contact with an outer portion 52 of the main body 26. Such deflection may occur upon insertion of the stopper 12 within the syringe barrel 16 to form an air pocket 53 to trap an air bubble therein. The air bubble trapped within air pocket 53 assists in the anti-reflux capabilities of the present invention as discussed in detail below. Upon insertion of the stopper 12 into the syringe barrel 16, the forward extending skirt 50 may be adapted to create a positive pressure within the syringe barrel 16.

In one embodiment, the main body 26 includes at least one undercut portion 55 extending axially inward from the open rearward end 28. The undercut portion 55 is adapted to engage the front forward end attachment portion 31 of the plunger rod 14 for locking the front forward end attachment portion 31 of the plunger rod 14 within the stopper 12. According to one embodiment, as shown in FIG. 3, the undercut portion 55 can include a reverse taper 56 adapted for cooperation with at least one deflecting arm 130 associated with the front forward end attachment portion 31 of the plunger rod 14.

The stopper 12 of the present invention may also be adapted to reduce and/or prevent mid-stream reflux. Mid-stream reflux occurs if the flush solution is not fully infused and the clinician does not clamp the line while the stopper is moving. Traditional syringe designs will generate reflux as the friction force on the stopper outer diameter and the plunger rod forces on the stopper center "stretch" the stopper nose. In order to overcome the static and dynamic friction to cause the stopper movement, the plunger rod force must be larger than the friction force, and this force imbalance is offset by the fluid back pressure and the stopper stretching. The difference is small, but measurable. As shown in FIG. 3 of the present application, a gap 94 is provided between a back portion 93 of the flexible core member 32 of the stopper 12 and the face 95 of the front forward end attachment portion 31 of the plunger rod 14. Because of this gap 94 and the flexibility of the flexible membrane 44 attaching the flexible core member 32 to the stopper main body 26, the flexible core member 32 is able to deflect proximally and store potential energy that is released in the form of positive displacement as soon as the plunger rod 14 force is ceased. Accordingly, during use of the syringe 10, due to gap 94, the plunger rod 14 does not directly apply a forward force to the flexible core member 32. Instead the plunger rod 14 applies a forward force to the interior side portion of the stopper 12 which, in turn, applies a pulling force to the flexible core member 32 via flexible membrane 44. Thus, during the application of pressure to the plunger rod, the flexible core member 32 is slightly retracted into the gap 94. Once the forward force is suspended, the flexible core member 32 continues this forward motion and prevents mid-stream reflux.

According to one aspect of the invention, as depicted in FIGS. 2B, 3, and 4B, the interior portion of the main body 26 includes an inner surface 132 having a taper 198 adapted for contact with a taper 196 on the front forward end attachment portion 31 of the plunger rod 14. These contacting tapers 196, 198 cooperate together such that the stopper 12 applies a radial force to the syringe barrel 16 to form an active seal therewith upon the application of a forward force to the plunger rod 14. The active seal aspect of the invention is discussed in detail below.

In accordance with a second embodiment of the invention, as illustrated in FIGS. 4A and 4B, the flexible membrane 44A may extend from the flexible core member 32 to the sidewall portion 57A of the main body 26 terminating at the first rib 46A. In one arrangement, the flexible membrane 44A, first rib 46A and sidewall 57A are integrally formed. In a further configuration, the forward extending skirt 50 of the first embodiment is not included.

Figure 5A:
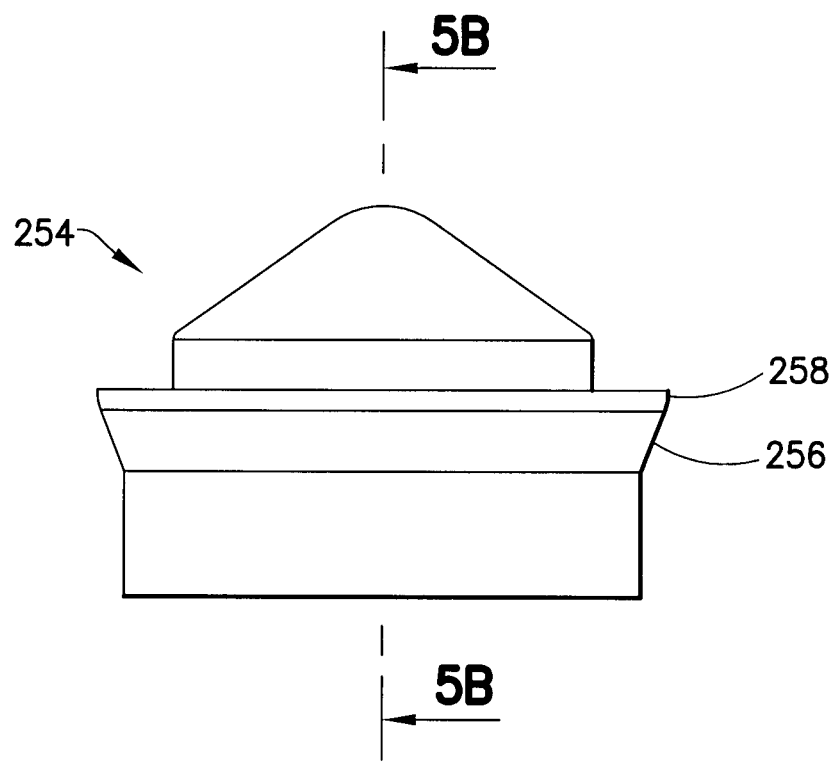
FIG. 5A is a side view of the stopper according to a third embodiment of the invention in accordance with an embodiment of the present invention.
Figure 5B:
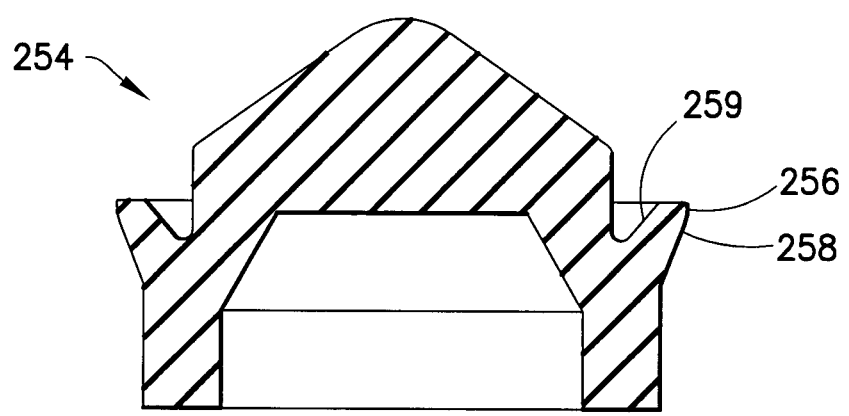
FIG. 5B is a cross-sectional view of the stopper taken along line 5B-5B of FIG. 5A.

According to a third embodiment of the invention, as illustrated in FIGS. 5A and 5B, an active seal achieves the same result as that of the previously discussed embodiments, but with a different mechanism, commonly referred to as a "Lip Seal" when used in hydraulic applications. The stopper, generally indicated as 254, includes this lip seal. The front seal 256 of the stopper 254 is located on the leading edge of a flexible arm 258. Initial sealing pressure is generated by the interference of the flexible arm 258 with the wall of the syringe barrel 16, as shown in FIG. 1. When the pressure in the syringe barrel 16 increases, this pressure applies an outward radial force to the inside 259 of the flexible arm 258. This outward force will increase the force with which the seal 256 presses against the inside wall of the syringe barrel 16.

Figure 6B:
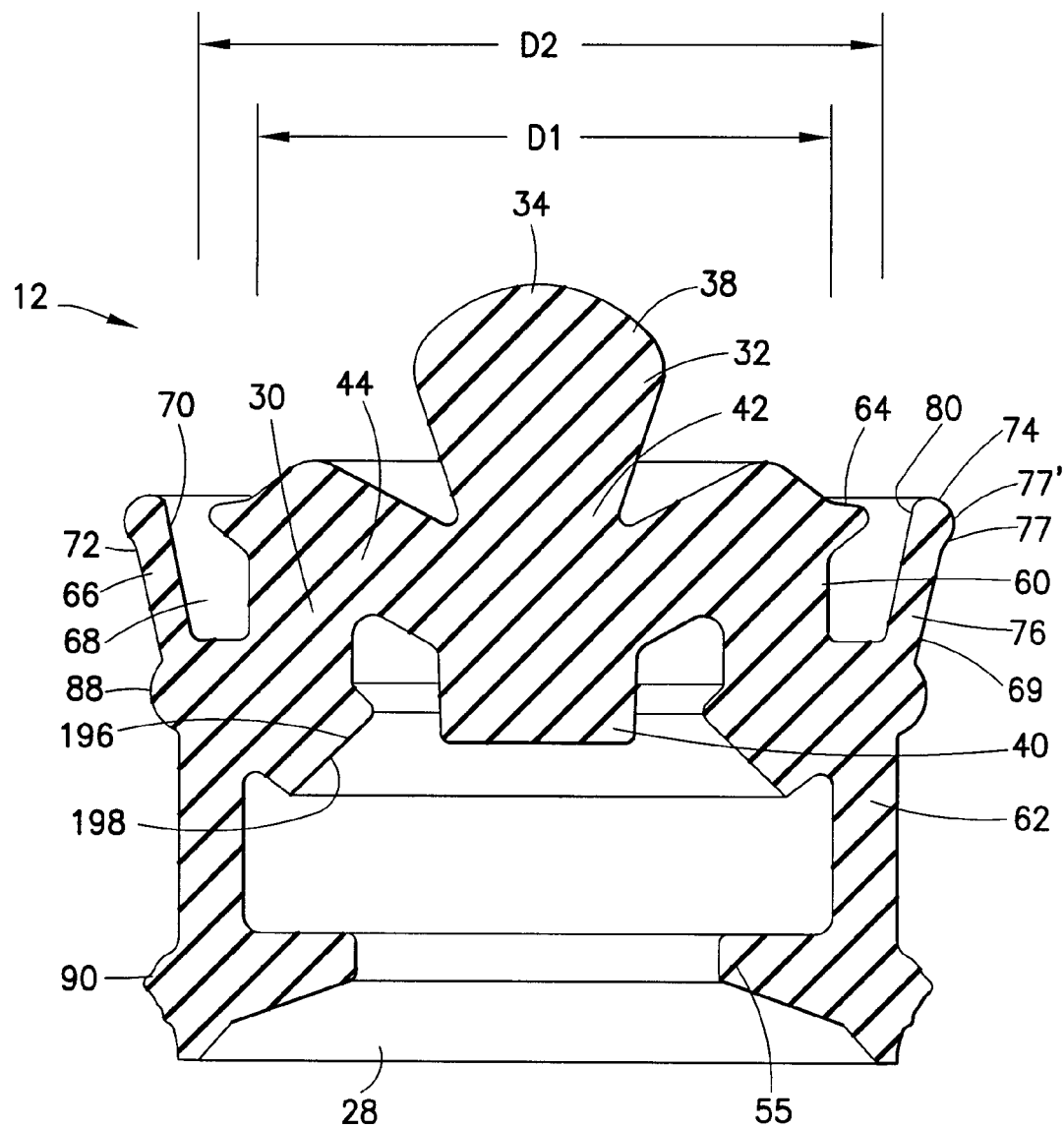
FIG. 6B is a cross-sectional side view of a stopper having an exterior design of FIG. 6A taken along line VI-VI of FIG. 6A and having an interior design according to the first embodiment of the invention shown in FIG. 2B.

Reference is now made to FIGS. 6A-6F and 7-9 which show the stopper 12 according to a fourth embodiment of the invention. In this embodiment, the stopper 12 includes a main body 26 having a closed front end 30. The main body 26 can include an open rearward end 28 which is adapted to receive a front forward end attachment portion 31 of the plunger rod 14. As stated above, the front forward end attachment portion 31 is capable of attachment to the stopper 12. The main body 26 includes a first body portion 60 having a first diameter D1, as shown in FIG. 6B, and a second body portion 62 having a second diameter D2, as shown in FIG. 6B, which is larger than the first diameter of the first body portion 60. A shoulder 64 extends around a perimeter of the first body portion 60 of the main body 26. Preferably, this shoulder 64 extends in a radially outward direction with respect to the first body portion 60.

As stated above with respect to the description of the first embodiment, a flexible core member 32 is integrally formed with the main body 26 adjacent the closed front end 30. The flexible core member 32 includes a nose portion 34 extending from the closed front end 30 which is adapted for contacting an interior surface 36 of an outlet opening, such as a luer 20 of the syringe barrel 16. The flexible core member 32 may be formed from a flexible material and the nose portion 34 may include a semi-spherical self-centering profile to create a positive seal with the luer 20 at the forward end of the syringe barrel 16.

Figure 7:
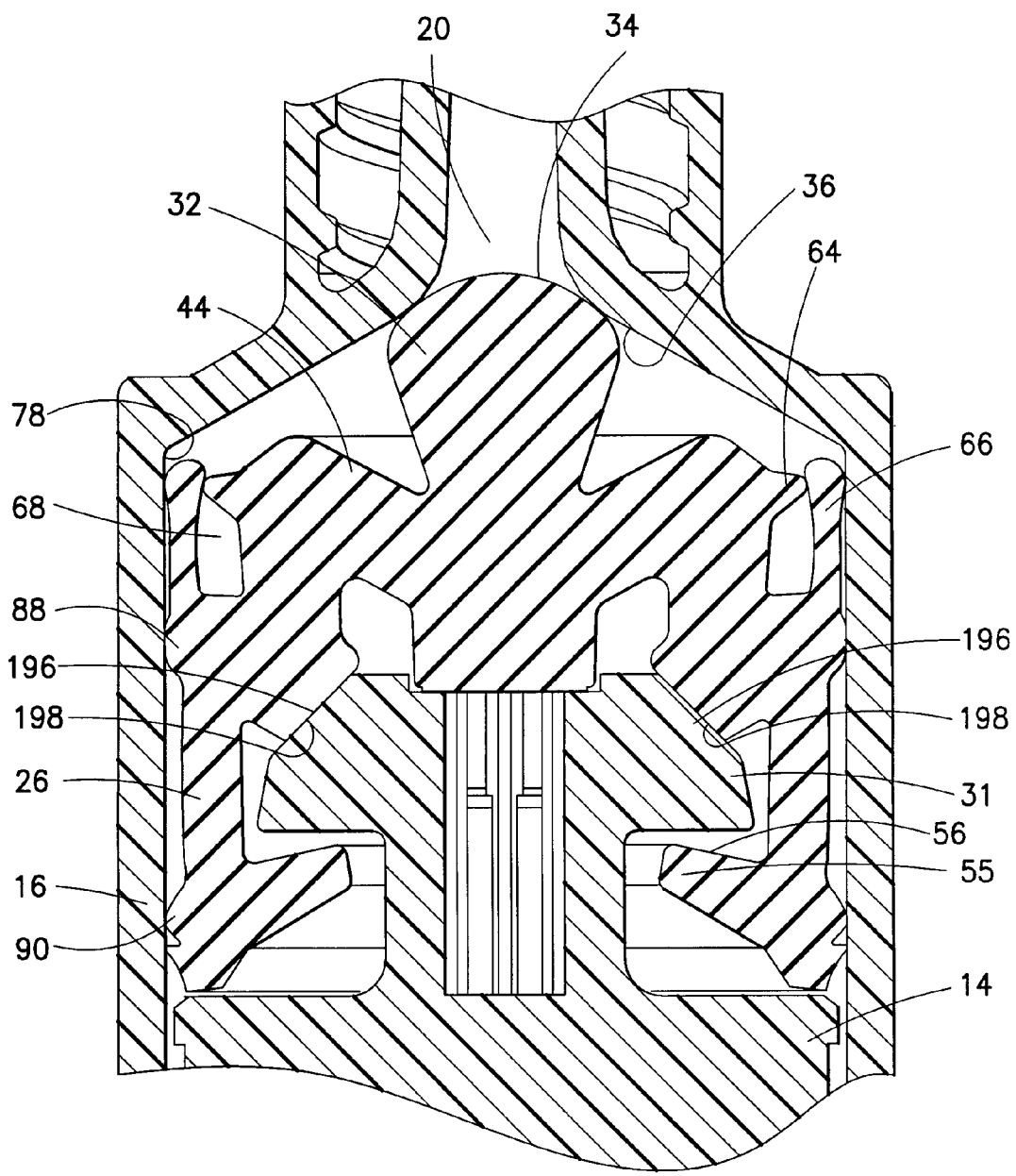
FIG. 7 is a cross-sectional side view of the stopper of FIG. 6B positioned within a syringe barrel.
Figure 8:
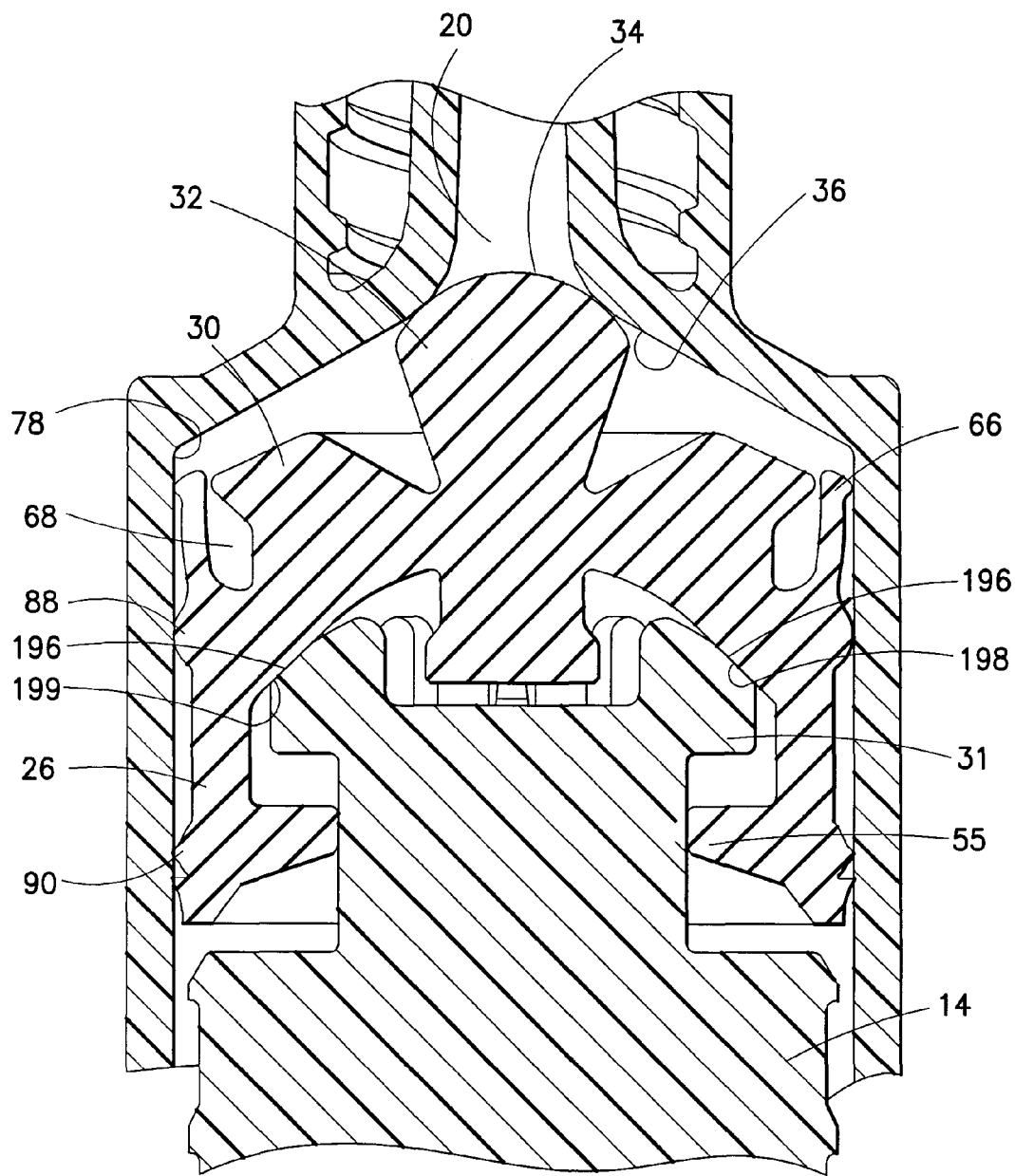
FIG. 8 is a cross-sectional side view of the stopper of FIG. 6C positioned within a syringe barrel.
Figure 9:
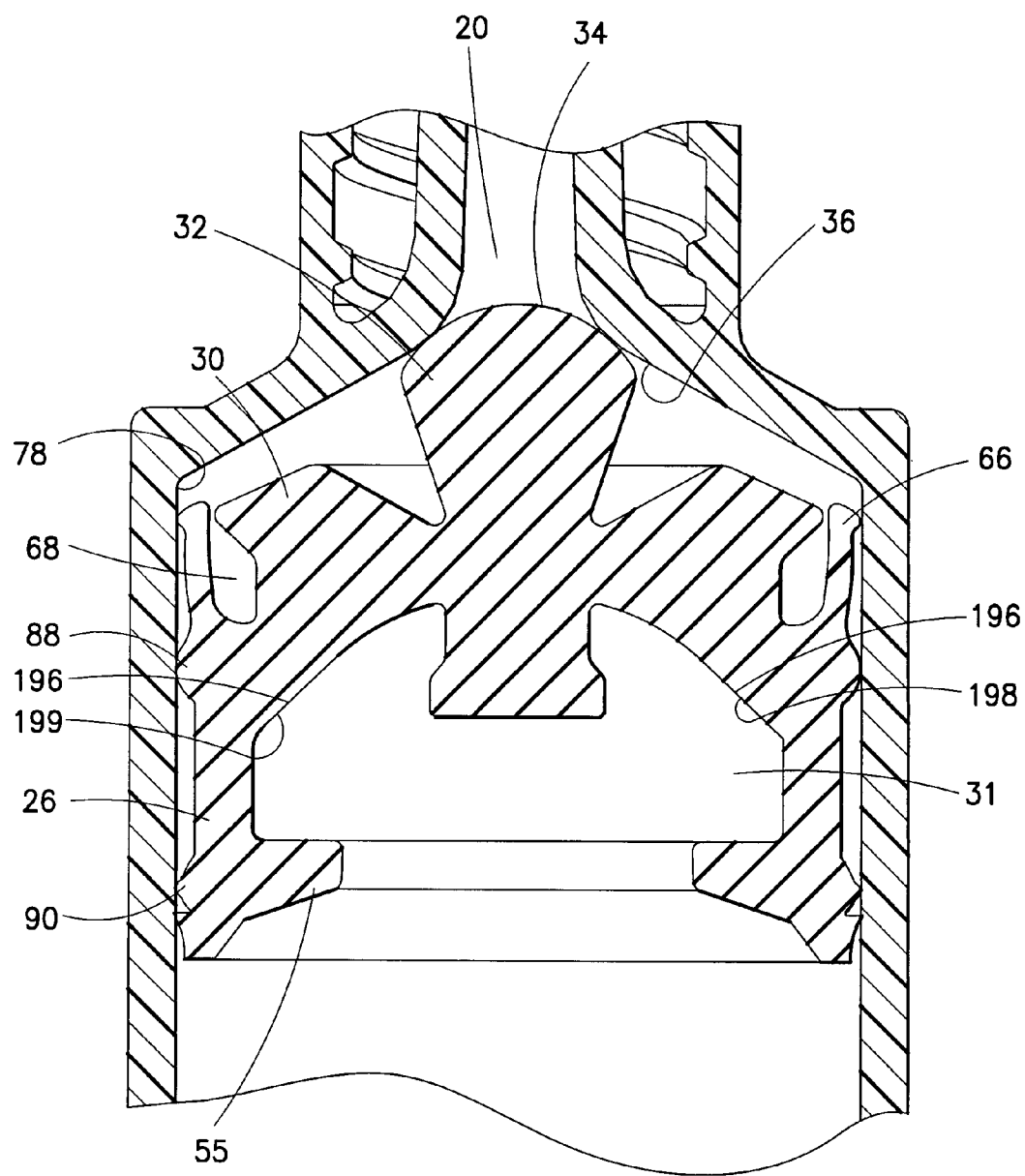
FIG. 9 is a cross-sectional side view of the stopper of FIG. 6D positioned within a syringe barrel.

The stopper 12 of the fourth embodiment, shown in FIGS. 6A-6E, differs from the first embodiment in that the stopper 12 includes at least one perimetrical skirt 66 extending from the second body portion 62 toward the front end 30 of the main body 26. This perimetrical skirt 66 cooperates with the shoulder 64 for trapping air pockets or an air bubble 68 therebetween upon insertion and/or movement of the stopper 12 within and through the syringe barrel 16. In this manner, upon release of a forward force on the plunger rod 14, fluid remaining within the syringe barrel 16 is forced through the luer 20 through positive displacement thereof. As shown in detail in FIGS. 6B-6D, the skirt 66 may include an inner surface 70 and an outer surface 72 and may be formed from a flexible and/or elastic material capable of deflecting radially inwardly. The inner surface 70 of the perimetrical skirt 66 may substantially contact the shoulder 64 to trap at least one air pocket/bubble 68. In one embodiment, the skirt 66 includes a lip portion 74 and a tail portion 76. The lip portion 74 may include an outwardly extending bump or first rib 77. An outer surface 77' of the first rib 77 may be adapted for contact with an inner surface 78 of the wall of the syringe barrel 16, shown in FIG. 1. This first rib 77 establishes a single line of contact between the perimetrical skirt 66 and the inner surface 78 of the wall of the syringe barrel 16, as shown in FIGS. 7-9. This first rib 77 functions to keep an outer surface 69 of the perimetrical skirt 66 adjacent the tail portion 76, positioned a predetermined distance apart from the inner surface 78 of the wall of the syringe barrel 16. This minimizes the area of contact between the perimetrical skirt 66 and the syringe barrel 16 to reduce break-loose forces and reduce static friction of the perimetrical skirt 66 with respect to the syringe barrel 16. The particular design of the perimetrical skirt 66 may allow for a clearer observation of the dose setting. In one embodiment, the perimetrical skirt 66 has a relatively linear shape and extends in a cylindrical manner about the first body portion 60 of the main body 26.

According to another embodiment, the inner surface 70 of the perimetrical skirt 66 does not necessarily contact the main body 26 to form the air pocket or chamber 68, but is close enough to the main body 26 such that surface tension keeps the chamber 68 closed off and traps an air bubble therein.

Figure 6C:
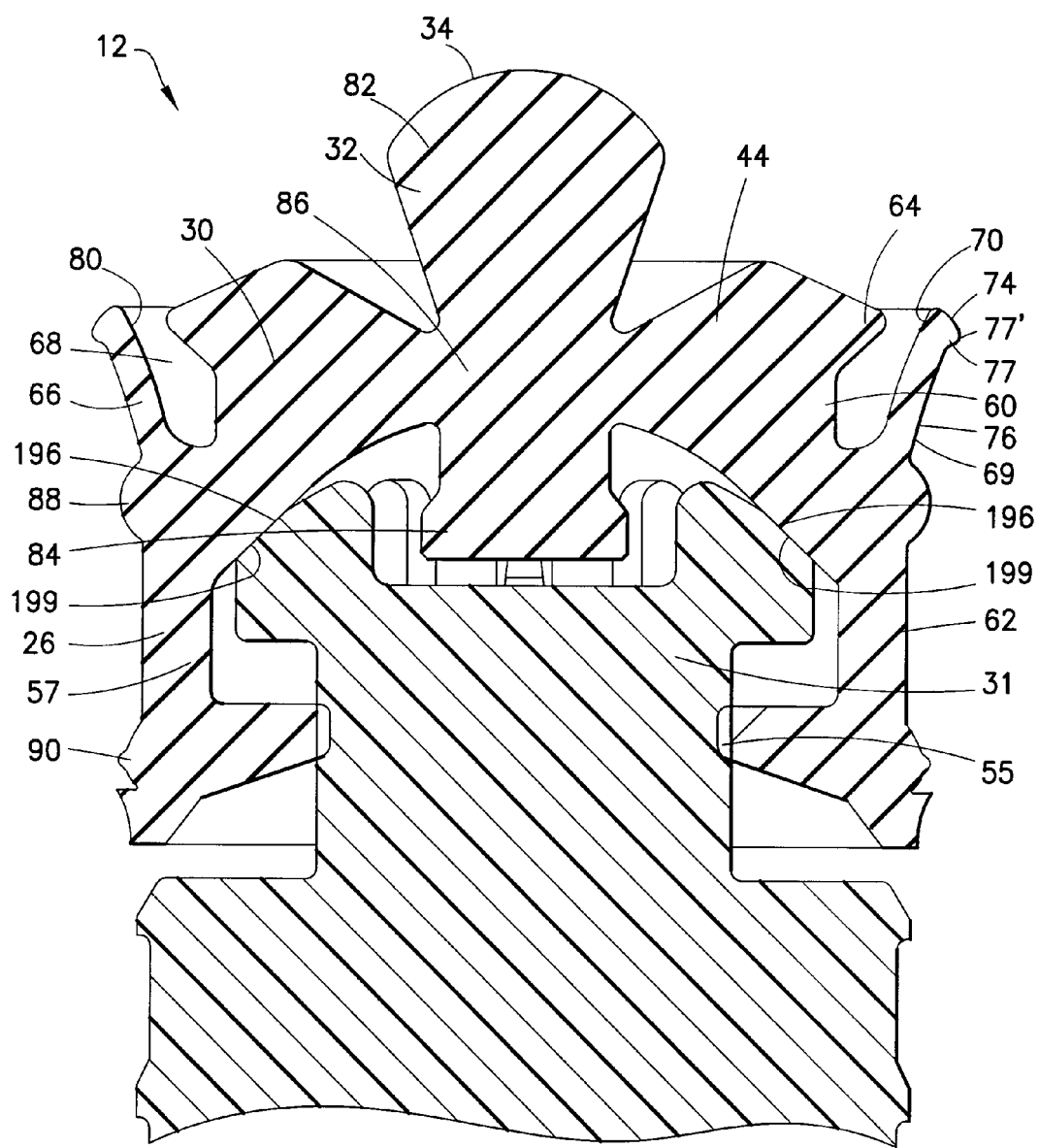
FIG. 6C is a cross-sectional side view of a stopper having an exterior design of FIG. 6A taken along line VI-VI of FIG. 6A and having an interior design according to the second embodiment of the invention shown in FIG. 4B in combination with one type of an attachment portion of a syringe plunger rod.
Figure 6D:
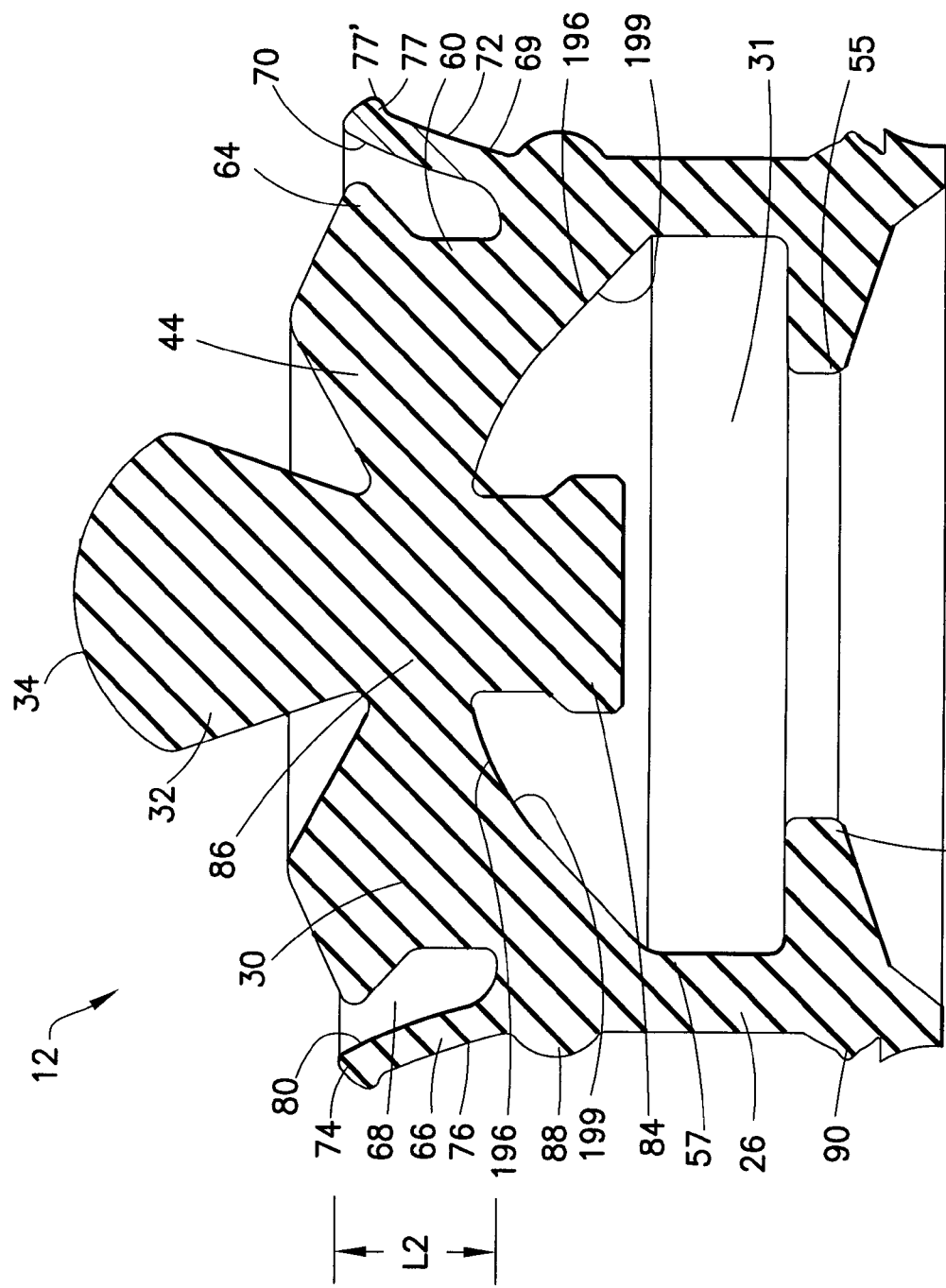
FIG. 6D is a cross-sectional side view of a stopper having an exterior design of FIG. 6A taken along line VI-VI of FIG. 6A and having an interior design as shown in FIG. 6C in combination with an alternative type of attachment portion of a syringe plunger rod.

As shown in FIGS. 6B-6D, the perimetrical skirt 66 of the stopper 12 is dimensioned to have a predetermined contact area 80 for cooperation with the shoulder 64. The contact area 80 is adapted for forming a predetermined gap sufficient for trapping air and allowing for communication of pressure from an air chamber to a fluid chamber.

Figure 6E:
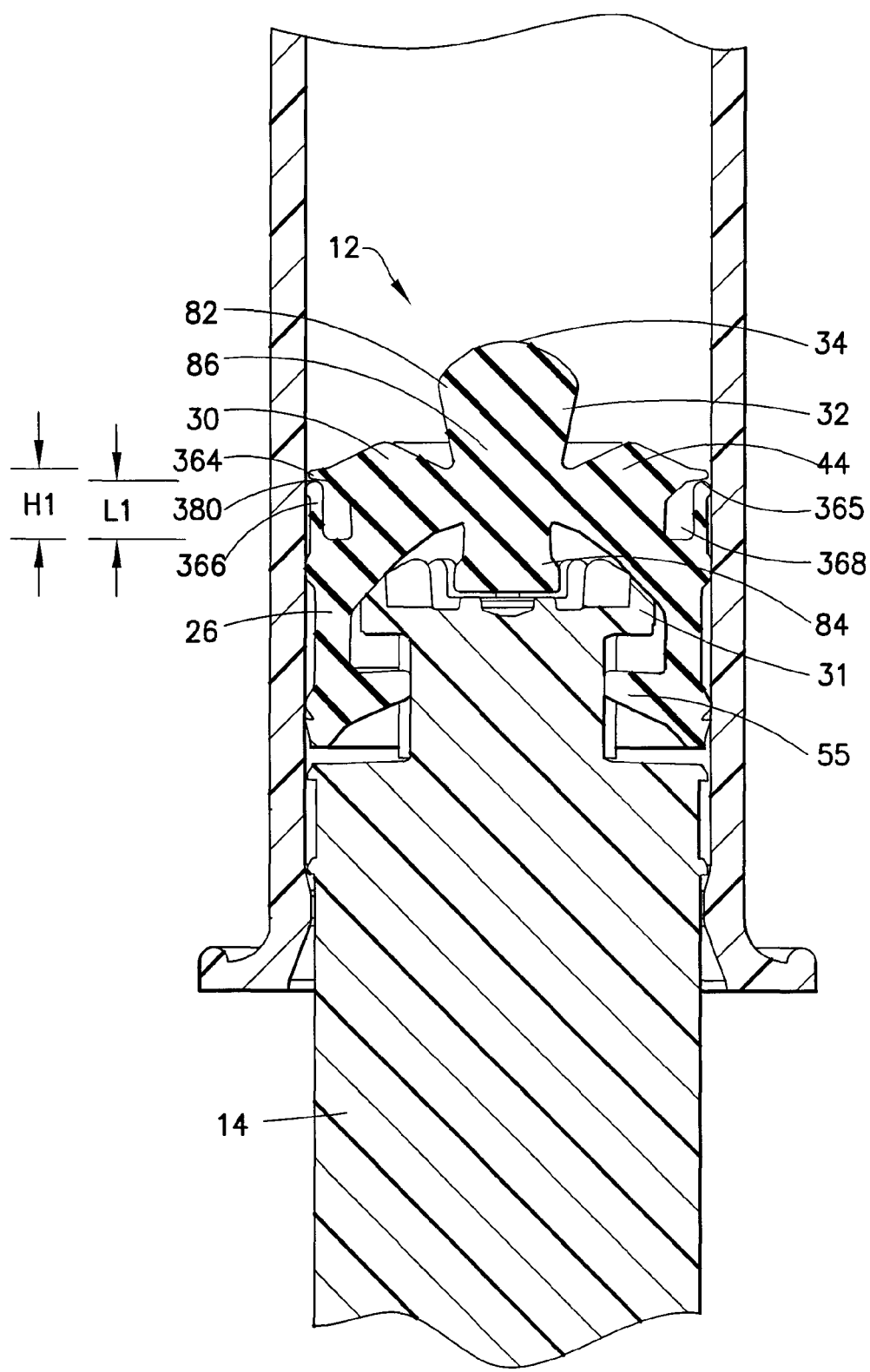
FIG. 6E is a cross-sectional side view of a stopper assembly having a modified skirt in accordance with an embodiment of the present invention.

FIG. 6E shows a modification of the stopper 12 of the fourth embodiment wherein the skirt 366 has a predetermined length L1 which is less than the length L2 of the perimetrical skirt 66 of FIGS. 6B-6D and less than the height H1 of the shoulder 364 such that the predetermined contact area 380 contacts a bottom surface 365 of the shoulder 364 to form the air pressure chamber 368.

Figure 6F:
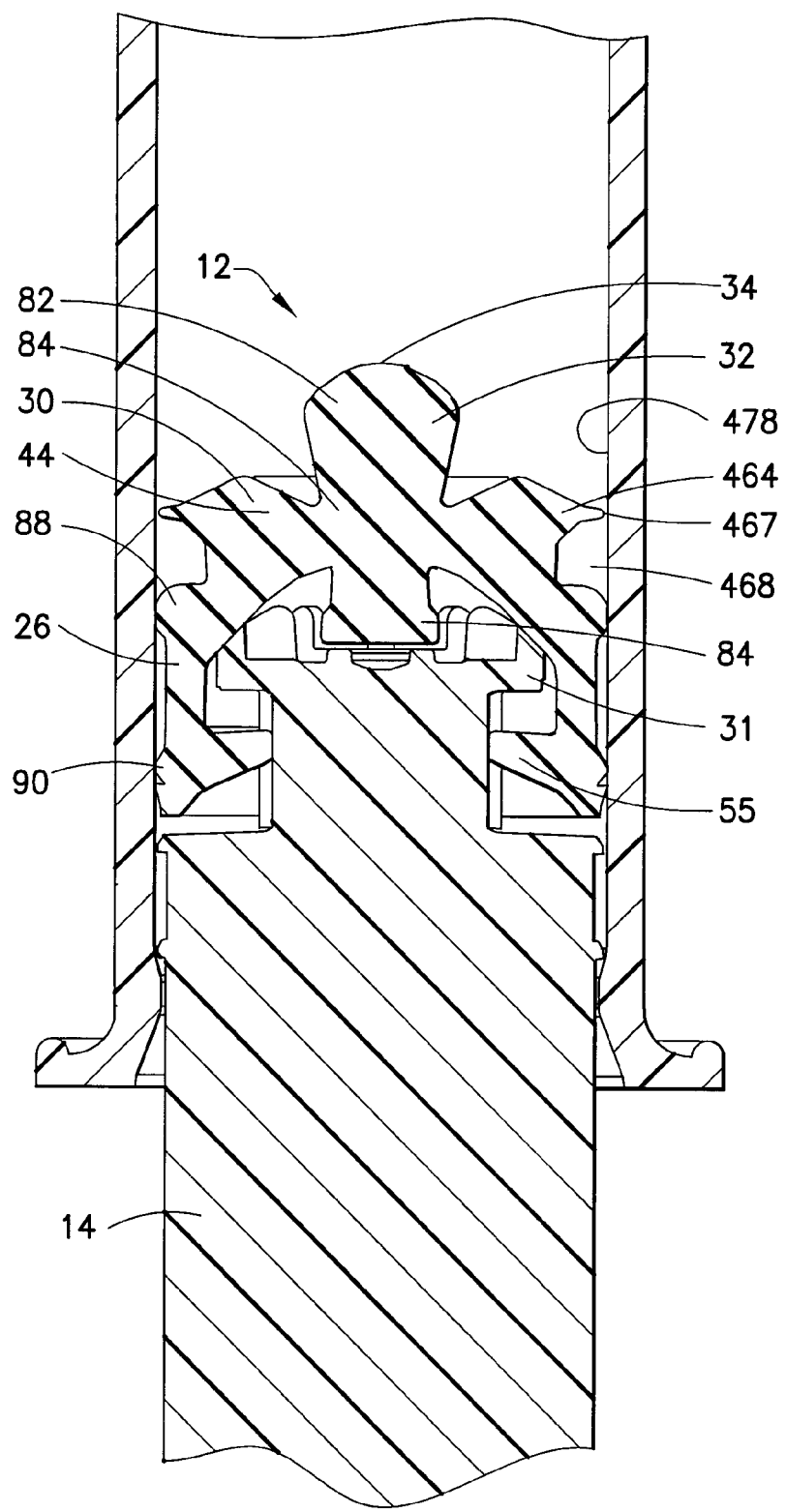
FIG. 6F is a cross-sectional side view of a stopper assembly in which the skirt has been eliminated in accordance with an embodiment of the present invention.

According to another arrangement, as shown in FIG. 6F, an air pressure chamber 468 can be created solely by the cooperation of the radially extending shoulder 464 with the inner surface 478 of the syringe barrel 416. In this configuration, the tip 467 of the shoulder 464 does not have to actually contact the inner surface 478 of the wall of the syringe barrel 16 in order to create the air pressure chamber 468, but rather only needs to be within a certain distance with respect to this inner surface to close off the air pressure chamber 468.

Referring again to FIGS. 6A-6F, the flexible core member 32 of the stopper 12 of the invention includes a front portion 82, extending above the main body 26, a back portion 84 and a central portion 86 positioned between the front portion 82 and back portion 84. The flexible core member 32 is interconnected with the main body 26 and, in particular, with the first body portion 60 thereof via a flexible membrane 44 extending between the central portion 86 of the flexible core member 32 and the first body portion 60 of the main body 26. The inventive design of the self-centering nose portion 34 allows for a seal to be made between the nose portion 34 and the interior surface 36 of an outlet opening or luer 20 when a small amount of force is applied to the stopper 12 and over the entire tolerance ranges of the stopper 12 through the plunger rod 14 and syringe barrel 16. As discussed above in relation to the first embodiment, the partially spherical surface shape of the nose portion 34 of the flexible core member 32 ensures full contact between the nose portion 34 and the interior surface 36 of the luer 20, even when the nose portion 34 has rotated or shifted prior to making contact.

The flexible membrane 44 and the air pocket/bubble 68 are adapted for storing potential energy such that upon release of a positive pressure on the plunger rod 14 and release of the seal between the nose portion 34 of the flexible core member 32 and the interior surface 36 of the luer 20, release of this potential energy forces fluid within the syringe barrel 16 through the luer 20 and any attached catheter.

According to the fourth embodiment of this invention, the main body 26 includes at least a second rib 88 extending substantially radially outward and substantially around a perimeter of the second body portion 62 of the main body 26. This second rib 88 is adapted to form an active seal with the inner surface 78 of the syringe barrel 16. The at least one air pocket/bubble 68 is positioned in a forward position with respect to the second rib 88. The main body 26 may include a third rib 90 such that the second rib 88 and third rib 90 extend radially outward around the perimeter of the outer diameter D2, as shown in FIG. 6B, of the second body portion 62 of the main body 26 and are axially spaced apart along this second body portion 62.

As shown in FIGS. 6B-6F and FIGS. 7-9, the main body 26 of the stopper 12 can include at least one undercut portion 55 extending axially inward of the open rearward end 28. This undercut portion 55 is adapted for locking the front forward end attachment portion 31 of the plunger rod 14 within the stopper 12. According to one aspect, the undercut portion 55 may include a reverse taper 56, as shown, for example in FIG. 7, which is adapted for cooperation with the front forward end attachment portion 31 of the plunger rod 14. Various designs of the front forward end attachment portion 31, according to the present invention are discussed in detail below.

As shown in FIG. 6B and FIG. 7, the main body 26 may also include an inner surface having a taper 198 adapted for contact with a taper 196 on the front forward end attachment portion 31 of the plunger rod 14. These contacting tapers 196, 198 cooperate together such that the stopper 12 applies a radial force to the syringe barrel 16 to form an active seal therewith upon the application of a forward force to the plunger rod 14.

According to another aspect of the invention, as depicted in FIGS. 6C, 6D, 8, and 9, the taper 199 of the inner surface 132 of the main body 26 may be a curved contour, which is continuous from a sidewall portion 57 of the main body 26 to the central portion 86 of the flexible core member 32. This continuous contour taper 199 is adapted for cooperating with taper 196 on the front forward end attachment portion 31 of the plunger rod 14 such that the stopper 12 applies a radial force to the syringe barrel 16 to form an active seal therewith upon the application of a forward force to the plunger rod 14.

An increase in pressure inside the syringe barrel 16 will cause the closed front end 30 of the stopper 12 to have a higher contact pressure with the inner surface 78 of the wall of the syringe barrel 16, thereby preventing leaks at the stopper 12 and syringe barrel 16 seal. The active seal of the present invention solves this problem by using a lower contact pressure between the stopper 12 and syringe barrel 16 when there are low fluid pressures in the syringe barrel 16, but higher contact pressure when the fluid pressure increases, such as during forward movement of the plunger rod 14 and stopper 12 through the syringe barrel 16.

In one embodiment, the active seal is achieved through the interaction of the front forward end attachment portion 31 of the plunger rod 14 and the inside of the stopper 12. According to one embodiment, as shown in FIG. 6B, the front forward end attachment portion 31 of the plunger rod 14 includes a forward leading surface taper 196 and corresponds to a taper 198 on the inside of the stopper 12. During use when the plunger rod 14 is being pushed, a forward leading edge applies force to the inside of the stopper 12. Due to the shape of the taper of the two surfaces 196, 198, the plunger rod 14 imparts a force that pushes the stopper 12 forward in the syringe barrel 16 and a force that pushes substantially outward in a radial direction. The outward force advances the stopper 12 forward of the second rib 88, and into the walls of the syringe barrel 16 which increases the sealing pressure. Likewise, as shown in FIGS. 6C and 6D, the taper 196 on the front forward end attachment portion 31 of the plunger rod 14 imparts a force to the continuous contour taper 199 of the inner surface 132 of the main body 26 such that the stopper 12 applies a radial force to the syringe barrel 16 to form an active seal therewith upon the application of a forward force to the plunger rod 14. High plunger rod forces are caused by high pressure in the syringe barrel 16, such that contact pressure therewith will increase as pressure in the syringe barrel 16 increases.

In a further embodiment, the perimetrical skirt 66 of the stopper 12 also acts as a lip seal. As the fluid pressure increases, increasing the air pressure in the air pocket/bubble 68, the skirt contact pressure at the interface of stopper 12 and syringe barrel 16 is increased, improving the sealing performance. Another advantage of this active seal is due to the application of the force of the plunger rod 14 only on the forward or second rib 88, which allows the back or third rib 90 to be "pulled" forward during injections. The pulling will also stretch the material of the back or third rib 90 reducing the effective force on the syringe barrel 16 and further reducing friction forces.

The stopper design of the present invention is intended to prevent reflux by creating positive displacement of fluid out of the front end of the syringe barrel (and into any attached catheter) after the stopper 12 has been bottomed in the syringe barrel 16 and force is released from the plunger rod 14. The features of the stopper 12 that act to create this positive displacement are the seal at the nose portion 34 of the stopper 12, the flex or relative movement of the stopper 12 between the nose portion 34 and the forward or second sealing rib 88, and potential energy in the form of pressurized fluid captured and stored prior to the release of the force from the plunger rod 14. The relative movement of the second rib 88, with respect to the nose portion 34 of the stopper 12, is achieved by means of the flexible membrane 44 that connects the outer forward or second rib 88, to the flexible core member 32 and nose portion 34. The energy storing is achieved by means of both the flexible membrane 44 and an air bubble or air pocket 68 that is trapped under the perimetrical skirt 66 just forward of the second rib 88.

The particular design of the fourth embodiment of the stopper 12 of the present invention has several advantages. For example, since the perimetrical skirt 66 may be substantially linear, without any radial flanges, wrinkling of the perimetrical skirt 66 is reduced and/or eliminated. In particular, the provision of the shoulder 64 on the first body portion 60 of the stopper main body 26 allows the perimetrical skirt 66 to have a relatively straight shape and the flexibility and/or elasticity of the perimetrical skirt 66 allows for flex in an inward direction to bring a contact area 80 of the perimetrical skirt 66, without deformation of the perimetrical skirt 66 itself, into contact with the shoulder 64. Another advantage of this design is that manufacturing of the stopper 12 is simplified. As only one molding tool plate is required for the bottom of the mold, the cost of the tooling is reduced.

The addition of the outwardly extending portion or bump 77 on the perimetrical skirt 66 minimizes the area of the perimetrical skirt 66 in contact with the inner surface 78 of the syringe barrel 16. This reduced contact area reduces break-loose forces and static friction and also provides a clear indication of the does setting. Finally, the design of the interference and length of the perimetrical skirt 66 is such to maintain the proper gap to trap air and allow for communication of pressure from the air chamber to the fluid chamber.

An active seal of the stopper 12 within the syringe barrel 16 can be further achieved by the front forward end attachment portion 31 of the plunger rod 14, as described below, in combination with the particular interior design of the stopper 12. The front forward end attachment portion 31 is adapted for use with any of the stopper embodiments previously disclosed herein. The invention is particularly useful in situations wherein the syringe 10 is pre-filled and sterilized and the stopper 12 is inserted into the syringe barrel 16 prior to attachment of the plunger rod 14 to the stopper 12.

As illustrated in FIGS. 16A-16C, the plunger rod 14 may include an elongated member 124 having a front end 126 and a back end 128 extending along a longitudinal axis AX, as shown in FIG. 16B. At least one deflecting arm 130 may be associated with the front end 126 of the elongated member 124. The deflecting arm 130 may be capable of deflecting radially inward during insertion of the plunger rod 14 into the stopper 12, and deflecting outward into contact with an inner surface 132 of the stopper 12, as shown in FIG. 3, after insertion into the stopper 12 to lock the plunger rod 14 within the stopper 12. FIGS. 16A-16C illustrate two deflecting arms 130, however, any number of deflecting arms 130 can be provided as needed to securely attach the plunger rod 14 within the stopper 12.

Referring back to FIG. 3, when the plunger rod 14 is inserted into the stopper 12, the deflecting arms 130 on the plunger rod 14 deflect and/or the stopper 12 deforms to allow the deflecting arms 130 to move into an undercut space 134 on the inside of the stopper 12. When the deflecting arms 130 enter the undercut space 134, the plunger rod 14 is locked in place and is prevented from separating from the stopper 12. When a user uses the syringe 10 to aspirate, the deflecting arms 130 on the plunger rod 14 will dig into the undercut surface 136 of the stopper 12, on the inside of the stopper 12, preventing the plunger rod 14 from pulling out of the stopper 12. The bottom surface 133 of the deflecting arm 130 can be tapered to correspond with the shape of the undercut surface 136 of the stopper 12. The deflecting arms 130 can be implemented according to several designs, as discussed in detail below.

Figure 17A:
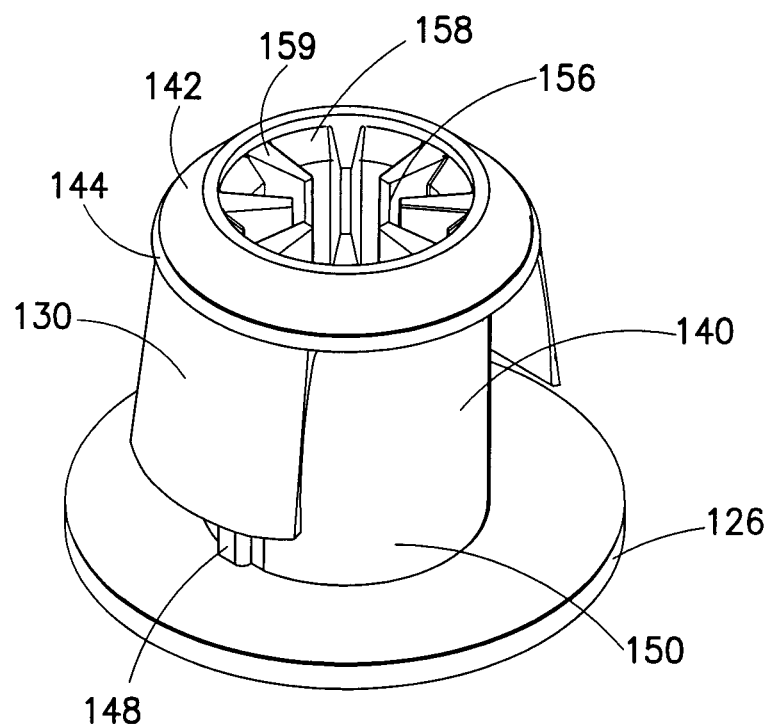
FIG. 17A is an enlarged perspective view of the attachment member for the plunger rod of FIG. 1 according to a first embodiment of the invention.
Figure 17B:
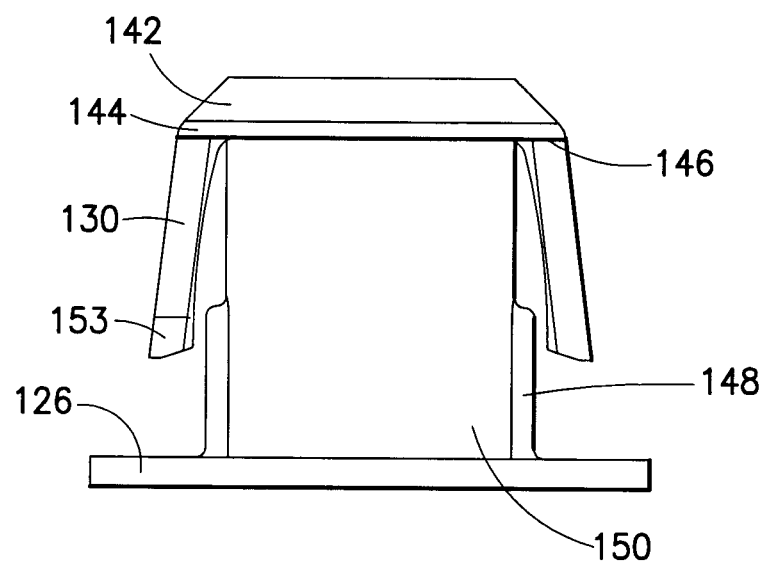
FIG. 17B is a side view of the attachment member of FIG. 17A.

According to a first embodiment, as illustrated in FIGS. 17A-17B, the front end 126 of the elongated member 124 includes a head member 140 extending from a front surface 144 of the front end 126. The head member 140 includes a rim member 142 extending along a front surface 144 thereof. The deflecting arms 130 may extend from a bottom surface 146 of the rim member 142 in a substantially downward direction. At least a first stop member 148 may be provided for limiting deflection of the deflecting arms 130 during insertion of the plunger rod 14 into the stopper 12. This first stop member 148 can be positioned adjacent to a rearward portion 150 of the head member 140.

The rim member 142 is preferably foil led from an elastomeric material capable of forming an active seal with an inside surface of the stopper 12, as shown in FIG. 3. A reinforcement material 153 may also be provided at the contact area of the deflecting arms 130. Also, as shown in FIGS. 16A, 16C, and 17A, the rim member 142 and head member 140 may include a hollow portion 156 defined by at least one sidewall 158. The sidewall 158 has a plurality of inwardly extending ribs 159 extending radially inward toward the center of the hollow portion 156. According to one embodiment, this hollow portion 156 can come into contact with a back portion of the flexible core member 32 inside of the stopper 12.

Figure 18A:
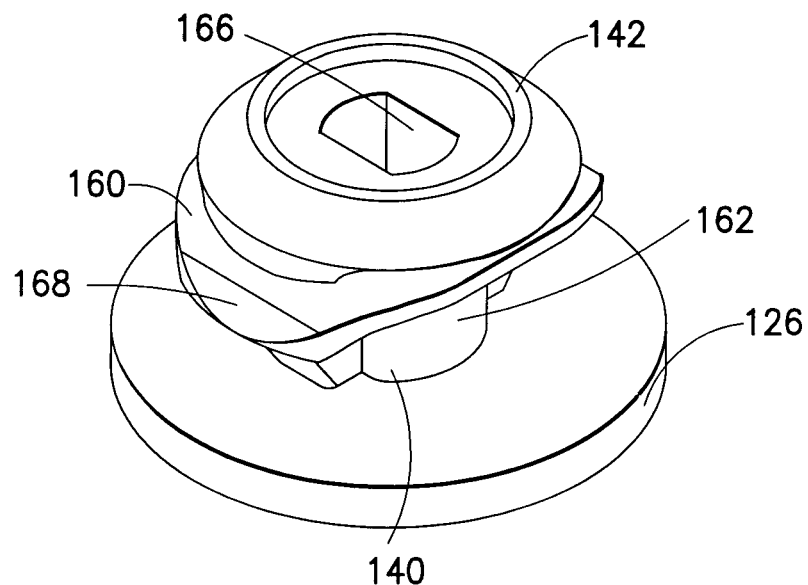
FIG. 18A is an enlarged perspective view of the attachment member for the plunger rod according to a second embodiment of the invention.
Figure 18B:
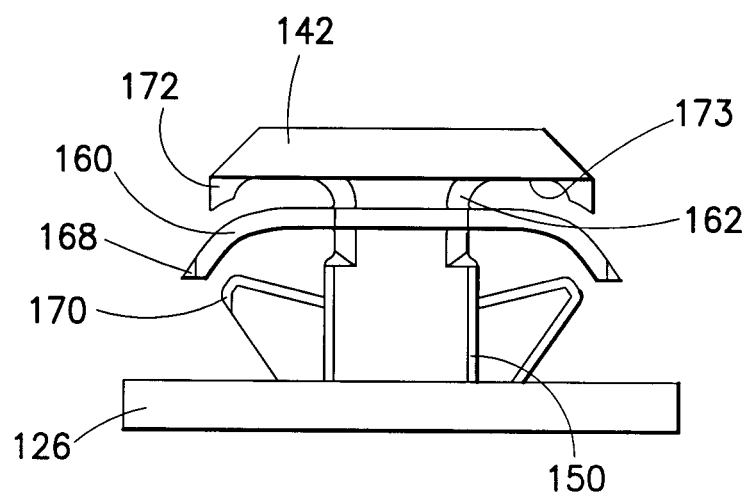
FIG. 18B is a side view of the attachment member of FIG. 4A.

According to a second embodiment, as illustrated in FIGS. 18A-18B, the at least one deflecting arm 160 extends radially outwardly from a center portion 162 of the head member 140. In this embodiment, the deflecting arm 160 may be a continuous member that extends through an aperture 163 in the center portion 162 of the head member 140. A hollow portion 166 is also provided in the head member 140 and rim member 142 of this embodiment. The edges 168 of the deflecting arm 160 may also be formed from appropriate reinforcement material. A first stop member 170 extends outward from a rearward portion 150 of the head member 140. A second stop member 172 extends rearward from a bottom surface 173 of the rim member 142 to limit arm deflection in an opposite direction, such as during aspiration of the syringe 10.

Figure 19A:
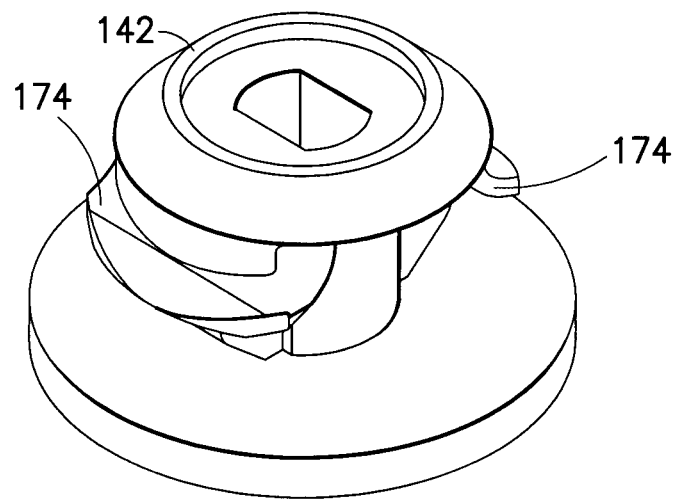
FIG. 19A is an enlarged perspective view of the attachment member for the plunger rod according to a third embodiment of the invention.
Figure 19B:
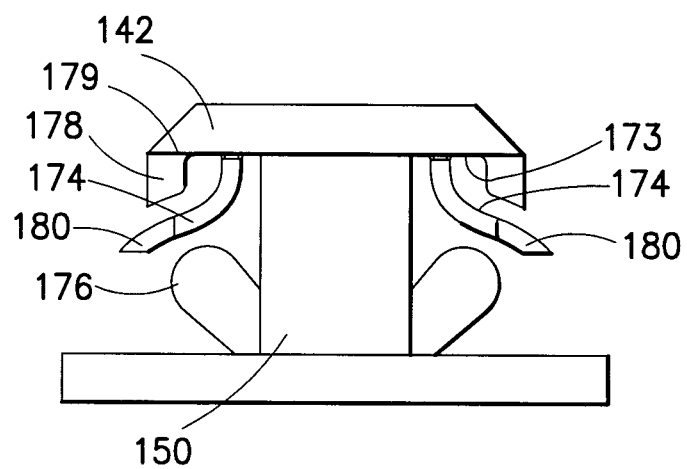
FIG. 19B is a side view of the attachment member of FIG. 19A.

According to a third embodiment, as illustrated in FIGS. 19A-19B, the at least one deflecting arm includes a pair of deflecting arms 174 extending in a downward and radially outward direction from the bottom surface 173 of the rim member 142. In this embodiment, a first stop member 176 extends outward from a rearward portion 150 of the head member 140. A second stop member 178 extends downward from an outer edge 179 of the rim member 142 for limiting deflection of the deflecting arms 174, such as during aspiration. The edges 180 of deflecting arms 174 are formed from appropriate reinforcement material.

Figure 20B:
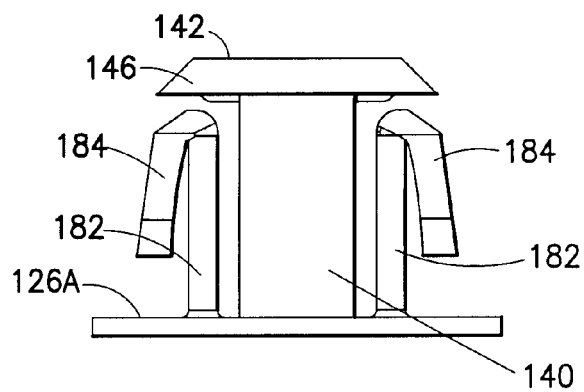
FIG. 20B is a side view of the attachment member of FIG. 6A.
Figure 20A:
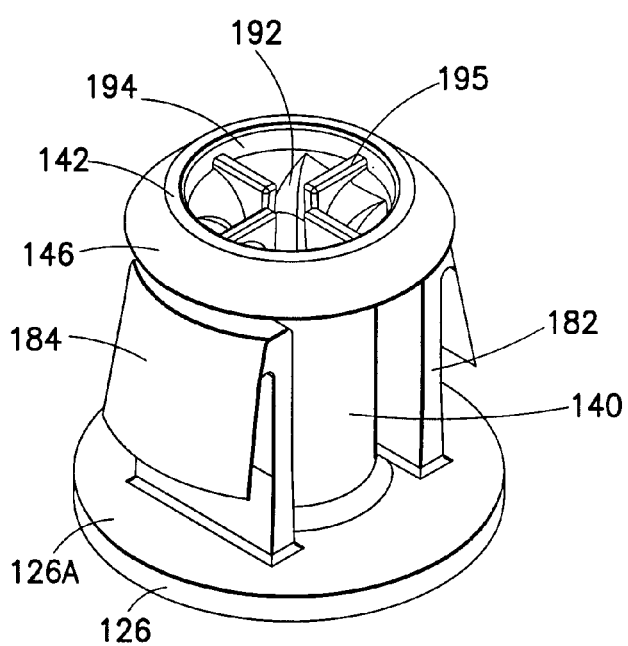
FIG. 20A is an enlarged perspective view of the attachment member for the plunger rod according to a fourth embodiment of the invention.
Figure 20C:
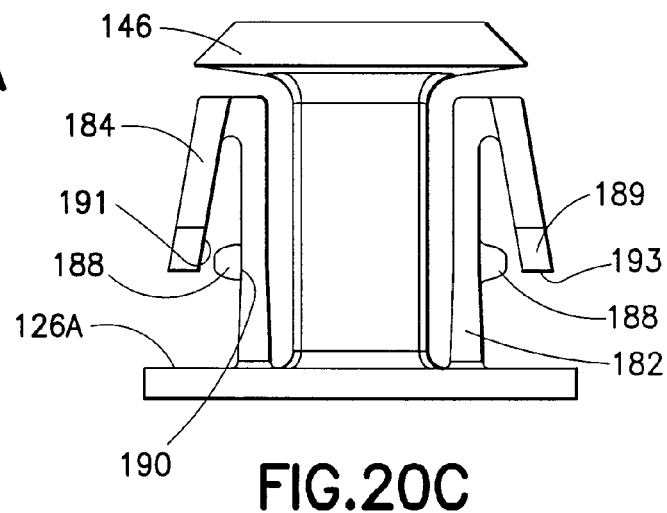
FIG. 20C is a side view of the attachment member of FIG. 6A including stop members.

According to a fourth embodiment, as illustrated in FIGS. 20A-20C, the front end 126 of the elongated member 124 includes a base surface 126A having a head member 140 extending therefrom. The head member 140 includes a rim member 142 extending along a front surface 144 thereof. In this embodiment, the at least one deflecting arm includes a first arm portion 182 extending from the base surface 126A parallel with the head member 140 and a second arm portion 184 attached to a front portion 186 of the first arm portion 182 extending in a rearward and outward direction with respect to the first arm portion 182. A stop member 188, as shown in FIG. 20C, may be provided to limit deflection of the second arm portion 184 during insertion of the plunger rod 14 into the stopper 12. This stop member 188 is positioned adjacent an outer surface 190 of the first arm portion 182 at a location adjacent to an inner surface 191 of the second arm portion 184. Portions of the second arm portion 184 may include a reinforcement material 189 as necessary. Additionally, the bottom surface 193 of the second arm member 184 may be flat or tapered as desired, depending upon the shape of the mating surface undercut portion 136 of the stopper 12.

These double deflecting arm portions 182, 184 can deflect from the base of the front end of the plunger rod 14 and from the top of the arm attached to the base of the front end geometry. During insertion, a normal load is exerted on the outside surface of the second arm portion 184. When the pressure is exerted at the top or front portion 186 of the second arm portion 184, first arm portion 182 deflects inwardly. As the pressure moves down the surface of second arm portion 184, this second arm portion 184 will begin to deflect. Deflection is greatest when both arm portions 182, 184 are at maximum deflection. During aspiration, a compressive and/or torsional load is exerted on the arm portions 182, 184 and the first arm portion 182 will begin to deflect inwards while second arm portion 184 digs into a stopper undercut surface, such as undercut surface 136, as shown in FIG. 3. Deflection, however, is limited by the contact between arm second arm portion 184 and the inner surface 132 of the wall of the stopper 12. As discussed above, a stop member 188 may be provided for reducing stresses on the arm portions 182, 184 by limiting the deflection of the arm portions 182, 184 where necessary, making deflection independent of the surface pressure during insertion and after the stop member 188 and second arm portion 184 are in contact with each other.

The FIGS. 20A-20C embodiment can also include an opening 192 in the head member 140 and rim member 142. This opening 192 is defined by a circular sidewall 194 and a plurality of ribs 195 extending inwardly from this circular sidewall 194 toward the opening 192.

Figure 21A:
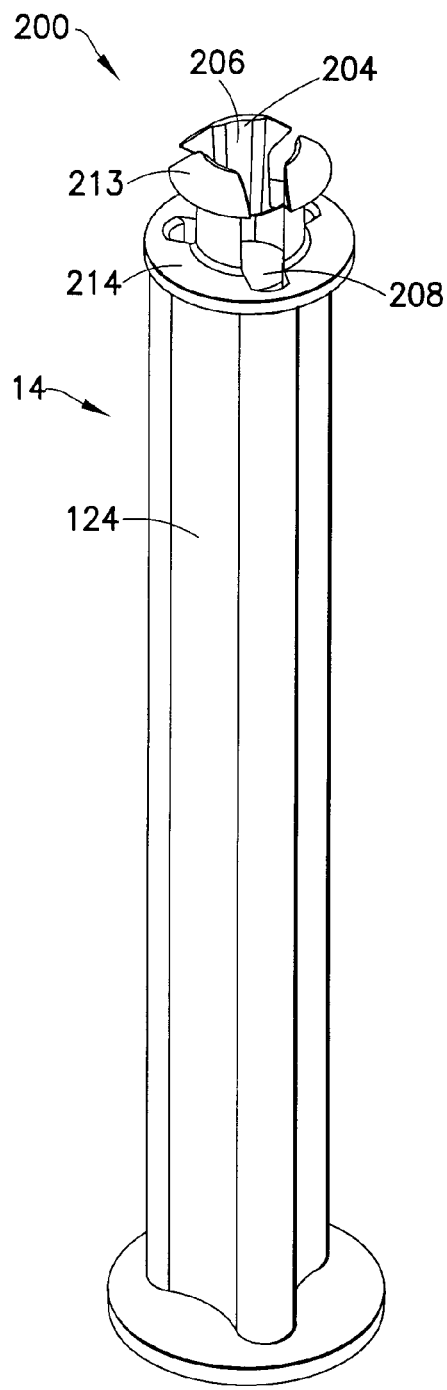
FIG. 21A is a perspective view of the plunger rod including an attachment member according to a fifth embodiment of the invention.
Figure 21B:
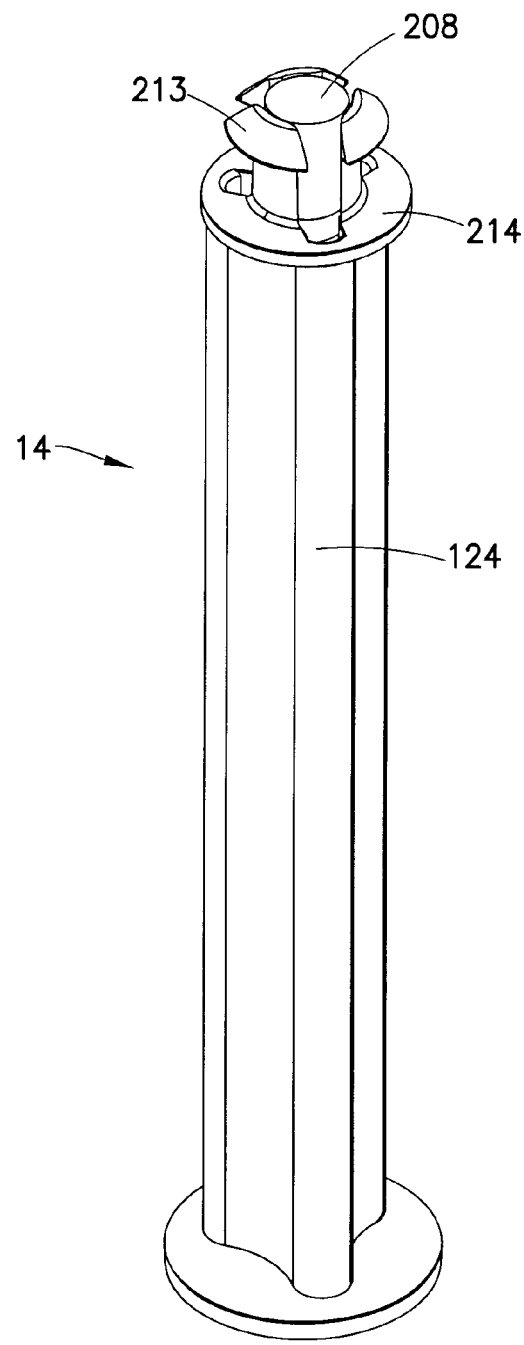
FIG. 21B is a perspective view of the plunger rod of FIG. 21A including a reinforcing slug located within the attachment member.
Figure 21E:
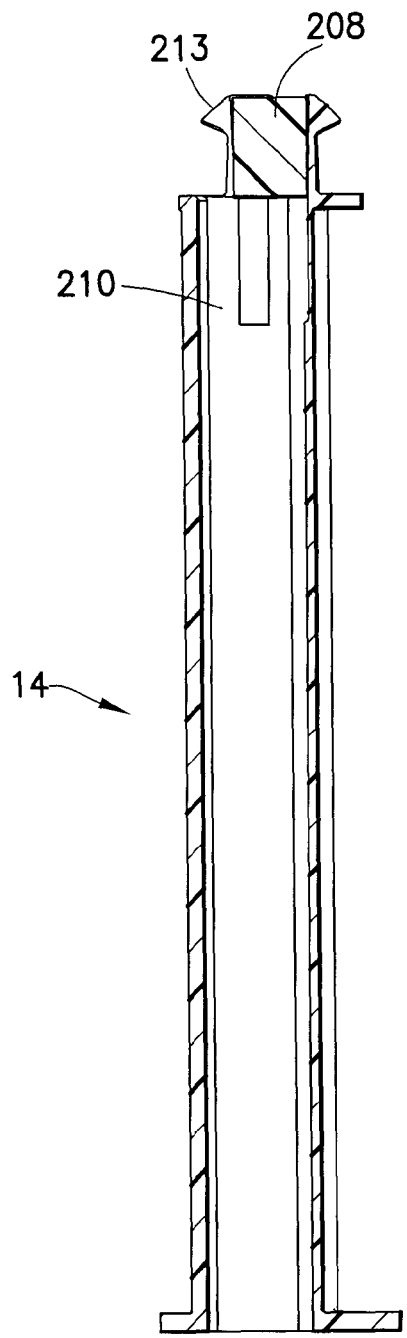
FIG. 21E is a cross-sectional side view taken along line 21E-21E of FIG. 21C.
Figure 21F:
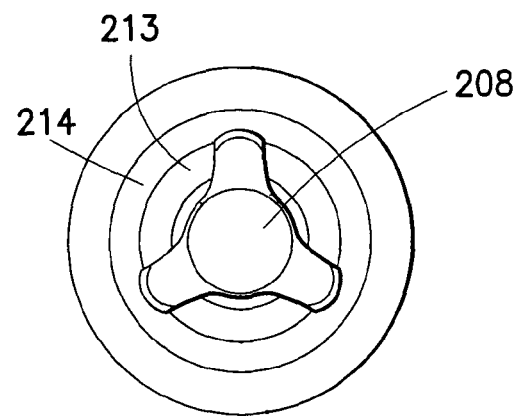
FIG. 21F is a top view of the attachment member of FIG. 21B.

According to a fifth embodiment, as illustrated in FIGS. 21A-21F, the attachment portion, generally indicated as 200, of the plunger rod 14 can include a deflecting arm 204 which can include a single circular deflecting arm or a plurality of deflecting arms extending from the front end 126 of the elongated member 124. This deflecting arm 204 defines a space 206, and during attachment of the plunger rod 14 within the stopper 12, the deflecting arm 204 deflects inwardly toward the space 206. When the deflecting arms 204 have reached maximum deflection and are housed in the undercut space 134 on the inside of the stopper 12, a slug 208 may be is inserted into this space 206 to support the deflecting arm 204 and prevent it from collapsing and separating from the stopper during use of the syringe 10. According to one embodiment, as illustrated in FIGS. 21D-21E, the elongated member 124 includes a hollow portion 210 and the slug 208 is pre-molded within this hollow portion 210. After the attachment of the plunger rod 14 to the stopper 12, an application force is applied within the hollow portion 210 to force the slug 208 into the space 206. Alternatively, the slug 208 may be separately molded and subsequently inserted.

Another aspect of the present invention is a new plunger body design as shown in FIGS. 22A-22B, 23A-23B, 24A-24B, and 25. The plunger rod 14 is preferably made of a rigid thermoplastic material. This design, as discussed in detail below, consists of a hollow elongated plunger rod body wherein the hollow portion is defined by a plurality of longitudinally extending lobes and preferably an odd number of lobes are provided. In traditional solid body four rib plunger designs, a user may apply a side load during aspiration that may be normal to the edge of a rib, causing minimal side loading deflection, or normal to the region in between the ribs, i.e., 45° from the rib, causing maximum side loading deflections. The present invention introduces a plunger body comprising an elongated body portion 234 having a front end 236, a back end 238, and a sidewall portion 239 extending along a longitudinal axis between the front end 236 and the back end 238. The sidewall portion 239 comprises a plurality of longitudinally extending lobes 240 defining an interior hollow portion 242. An attachment member 244 is secured to the front end 236 and is adapted for attachment of the plunger rod 14 to the stopper 12. A cover member 246 is secured to the back end 238 of the elongated body portion 234 for covering the interior hollow portion 242 and providing a thumb press area 248 for application of a force to the plunger rod 14 during use.

Figures 22A, 22B:
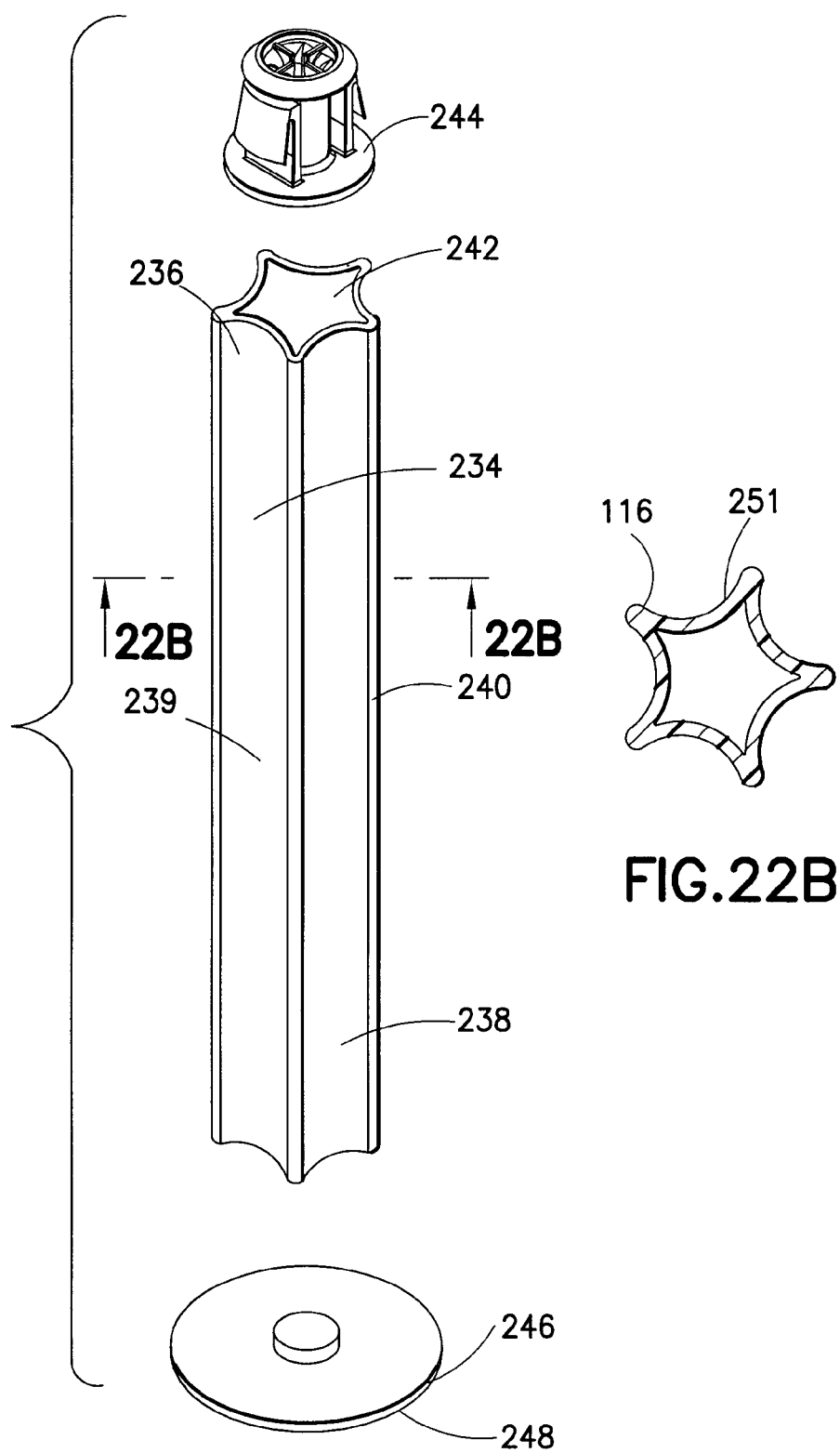
FIG. 22A is an exploded perspective view of the plunger rod according to one embodiment of the invention.
FIG. 22B is a cross-sectional view of the plunger rod of FIG. 21A taken along line 22B-22B.

The longitudinally extending lobes 240 preferably comprise an odd number of lobes spaced substantially equidistant with respect to one another. According to one embodiment, as shown in FIGS. 23A-23B, the plurality of longitudinally extending lobes 240 comprises a three lobe design 250 positioned at approximately 120° with respect to one another. According to still another embodiment, as shown in FIGS. 22A-22B, the plurality of extending lobes 240 number at five, forming a five lobe design 251 wherein the lobes 240 are spaced substantially equidistant with respect to one another. The lobes are positioned with respect to one another to form substantially uniform side loading deflection of the plunger rod 14. Providing an odd number of lobes 240 decreases the expected deflection when a load is applied to the region between the lobes 240 by introducing a lobe on the opposite side which supports the reaction load. The present invention also includes four lobe 240 hollow elongated plunger body designs 252, such as illustrated in FIGS. 24A-24B. Because the body portion of the plunger 14 includes a hollow portion 253, the advantages associated with the hollow design, as discussed above, would also be present in the four lobe design 252. The hollow design also provides additional stiffness to the body portion 234 of the plunger rod 14 and several ergonomic improvements, such as reduced product costs, easier manufacturing procedures, and the like as discussed in detail below.

The plunger rod 14 of the invention may be manufactured according to the following processes. In a first process, the elongated body portion 234 and the front end attachment member 244 are integrally molded from the same material. The plunger rod 14 is designed to have an interior hollow portion 242 so that a core pin can be driven up the center of the plunger rod 14 during injection molding. This allows the plunger rod 14 to be molded "standing up", which results in a reduction in cycle time due to additional cooling in the core pin and an increase in volume due to an increase in cavity number. To cover the core pin opening or interior hollow portion 242 on the thumb press side/area 248, a soft-touch surface disk 249 may be attached to the thumb press area 248 for added comfort during injection.

According to a second process, as shown in FIG. 25, the plunger rod 14 can be manufactured in three separate pieces. The attachment member 244 can be injection molded, the elongated body portion 234 of the plunger rod 14 can be extruded or injection molded, and the cover member or thumb press disk 246 can be manufactured by a stamp molding process. The attachment member 244, elongated body portion 234, and thumb press disk 246 can be formed from different materials for improved performance where needed. For example, a more expensive material may be used to mold the front attachment member 244 for improved performance and a soft touch elastomer may be used for the thumb press disk 246. Extruding the body portion 234 of the plunger 14 allows for additional cross section geometries that would provide uniform side loading deflection and allow for ergonomic improvements that would other wise be limited by parting lines on the mold. Additionally, using an extrusion process for the body portion allows for the production of body portions of different lengths for use with different length syringe barrels 16 from a single extrusion device.

In the attachment arrangements of FIGS. 17A-17B, 18A-18B, 19A-19B, and 20A-20C, each of these embodiments include a head member 140 having a rim member 142 extending along a front surface 144 thereof wherein the rim member includes a taper 196 adapted for contacting a corresponding taper 198, within the stopper 12, as shown in FIG. 2B for applying a radial force to the stopper 12 upon the application of a forward force to the plunger rod 14. In the FIG. 21A-21F arrangement, the deflecting arm 204 includes a taper 213 at a forward end 214 thereof adapted for contacting a corresponding taper 198 within the stopper 12 for applying a radial force to the stopper 12 upon the application of a forward force to the plunger rod 14.

The stopper design of the present invention is intended to prevent reflux by creating positive displacement of fluid into the attached catheter after the stopper 12 has been bottomed in the syringe barrel 16 and force is released from the plunger rod 14. The features of the stopper 12 that act to create this positive displacement are the seal at the nose portion 34 of the stopper 12, the flex or relative movement of the stopper 12 between the nose portion 34 and the forward or first sealing rib 46, and a means by which potential energy in the form of pressurized fluid can be captured and stored prior to the release of the force from the plunger rod 14. The relative movement of the first rib 46 with respect to the nose portion 34 of the stopper 12 is achieved by means of the flexible membrane 44 that connects the outer first rib 46 to the flexible core member 32 and nose portion 34. The energy storing is achieved by means of both the flexible membrane 44 and the air bubble or air pocket chamber 53 that is trapped under the folded forward extending skirt 50 just forward of the first rib 46.

Figure 10:
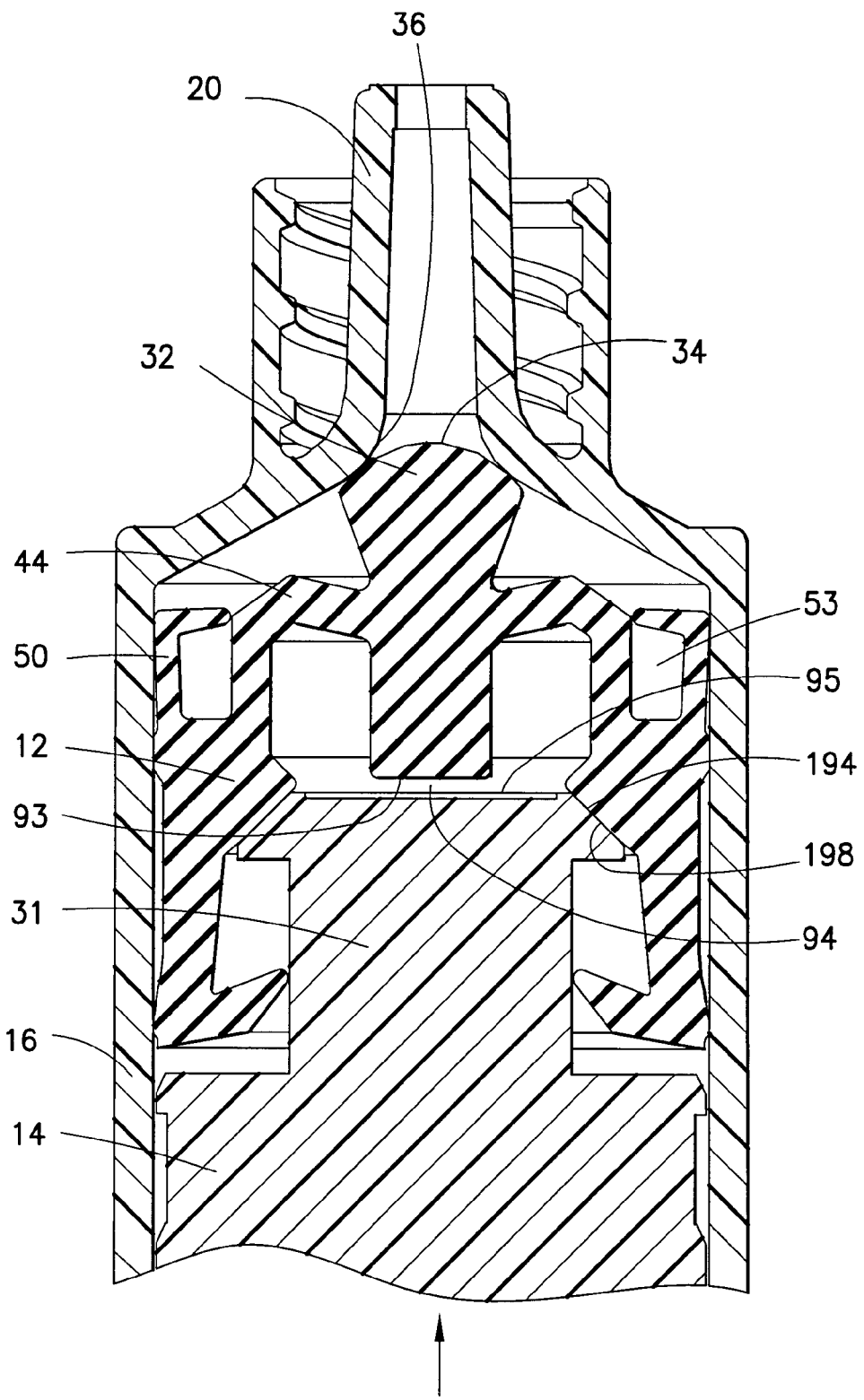
FIG. 10 is a cross-sectional side view of a stopper/plunger arrangement utilizing the stopper of FIG. 2B during a first reflux reduction step of the invention.
Figure 11:
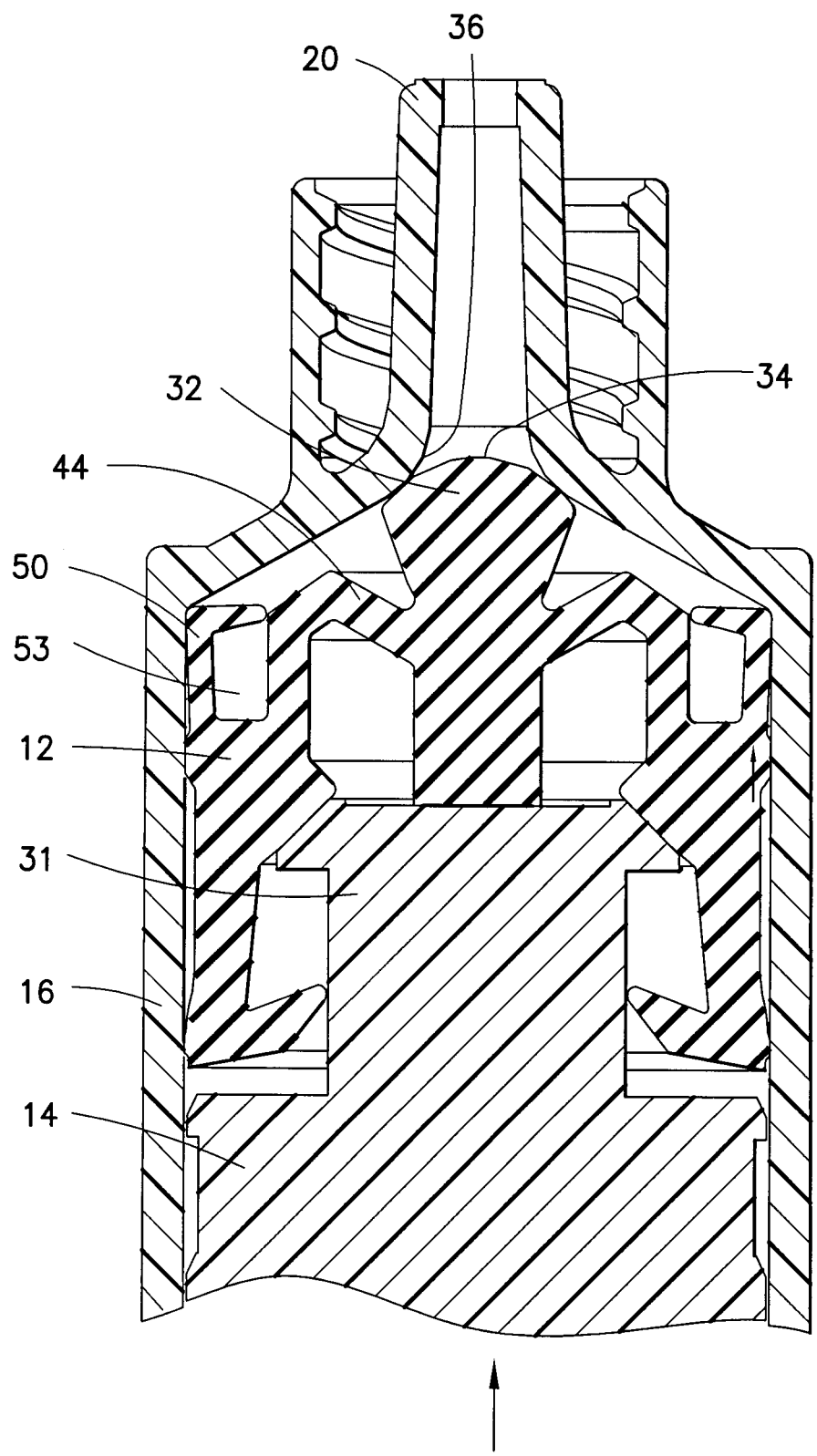
FIG. 11 is a cross-sectional side view of a stopper/plunger arrangement utilizing the stopper of FIG. 2B during a second reflux reduction step of the invention.
Figure 12:
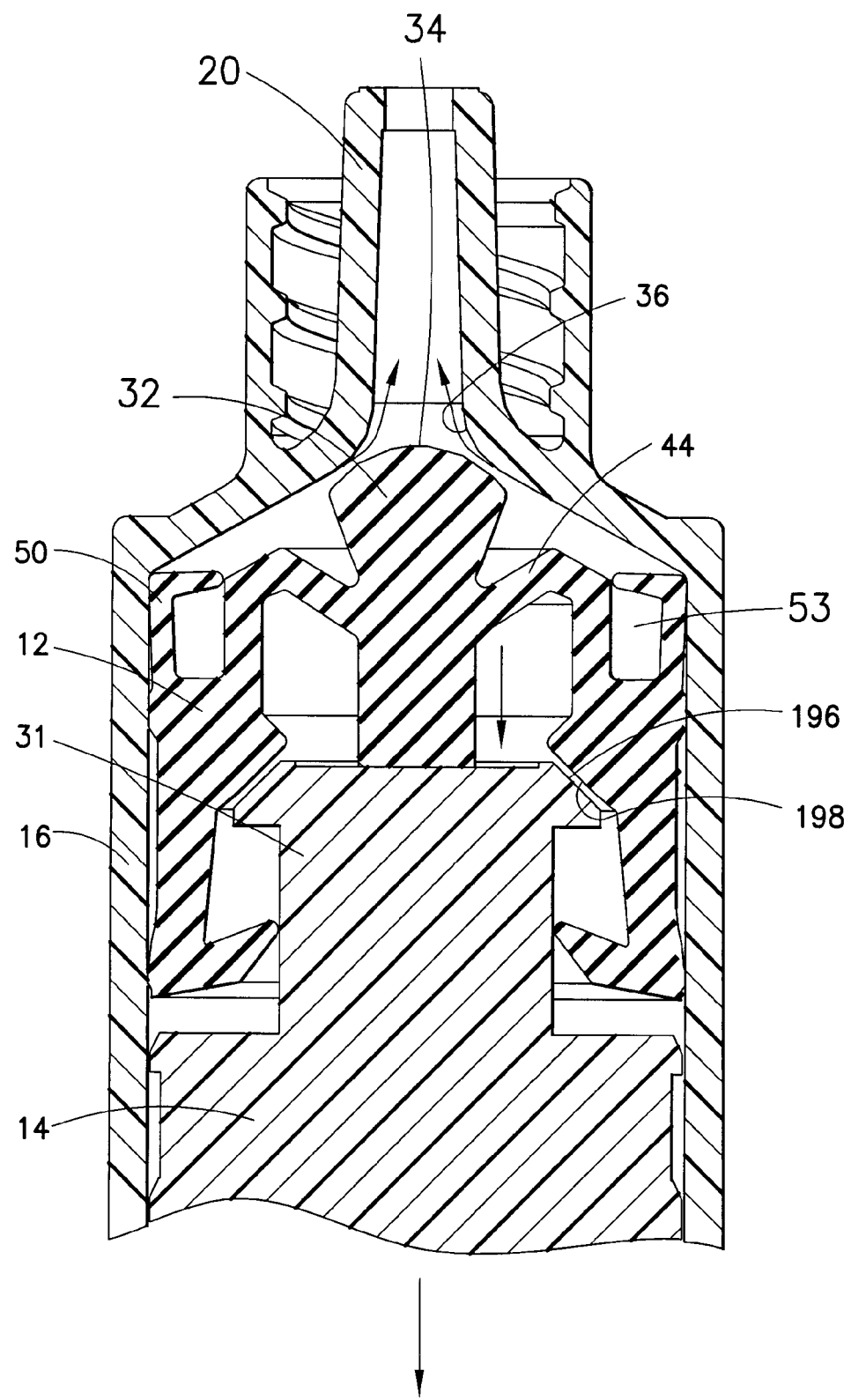
FIG. 12 is a cross-sectional side view of a stopper/plunger arrangement utilizing the stopper of FIG. 2B during a third reflux reduction step of the invention.

As illustrated in FIGS. 10-12, positive displacement or a method of preventing reflux within the syringe barrel includes the following steps. The first step provides a stopper 12 having a main body defining an open rearward end 28 and a closed front end 30. The open rearward end 28 is adapted to receive a front forward end attachment member 31 of a plunger rod 14 therein. A flexible core member 32 is interconnected with the main body 26 via a flexible membrane 44 integrally formed with the main body 26 adjacent the closed front end 30. The flexible core member 32 includes a nose portion 34, preferably having a profile, as discussed above, which is self-centering and adapted to create a positive seal with an interior surface of the luer 20 of the syringe barrel 16. The method further includes the step of inserting the front forward end attachment member 31 of the plunger rod 14 within the open rearward end 28 of the stopper 12. Applying a force to the plunger rod 14 to advance the stopper 12 into the syringe barrel 16 until the nose portion 34 of the flexible core member 32 contacts the interior surface 36 of the syringe barrel luer 20 forming a seal and trapping fluid from flowing into the luer 20. Applying additional force to the plunger rod 14 to compress the nose portion 34, advances the at least one rib 46 within the syringe barrel 16 and compresses the trapped air to form increased pressure within the air pocket 53. The final step of the method comprises releasing the force on the plunger rod 14 to release the seal between the nose portion 34 and the interior surface 36 of the luer 20 wherein friction force maintains the rib 46 in an advanced position within the syringe barrel 16 such that the increased pressure within the air pocket 53 causes any trapped fluid to be pushed through the luer 20 and any attached catheter.

FIGS. 2A-2B and 3 show a stopper design wherein the stopper 12 includes at least one forward extending skirt 50 extending from a closed front end 30 of the main body 26 and wherein the step of applying a force to advance the stopper 12 into the syringe barrel causes this skirt 50 to deflect inward with respect to the main body 26 of the stopper 12 to substantially contact, or to within a predetermined distance with respect to an outer portion 52 thereof, to form an air pocket 53 for trapping air therein. The step of applying additional force to the plunger rod 14 to compress the nose portion 34 causes the flexible membrane 44 to stretch. The step of releasing the force on the plunger rod 14, thereby releases the force on the flexible membrane 44, causing any trapped fluid to be pushed through an outlet opening or luer 20 and any attached catheter.

FIGS. 4A and 4B show a stopper design which does not rely on a flexible skirt to trap an air bubble to assist in storing energy to force any trapped fluid through the luer 20. Rather, this design only relies on the flexibility of the membrane 44A connecting the flexible core member 32 to the main body 26 of stopper 12 to capture pressure energy and return it once force is released from the plunger rod 14. Additional features that can trap an air bubble include other forms of molded-in pockets or slotted channels in the stopper face.

FIGS. 5A and 5B illustrate yet another design of the stopper 254, according to the invention. This design, discussed in detail above, shows a lip seal for sealing against the barrel. The front seal 256 of the stopper 254 is located on the leading edge of flexible arm 258. The initial sealing pressure is generated by the arm's interference with the barrel wall. When the pressure in the syringe barrel 16 increases, an outward radial force is applied to the inside 259 of the flexible arm 258. This outward push will increase the force with which the seal presses against the barrel wall.

Figure 13:
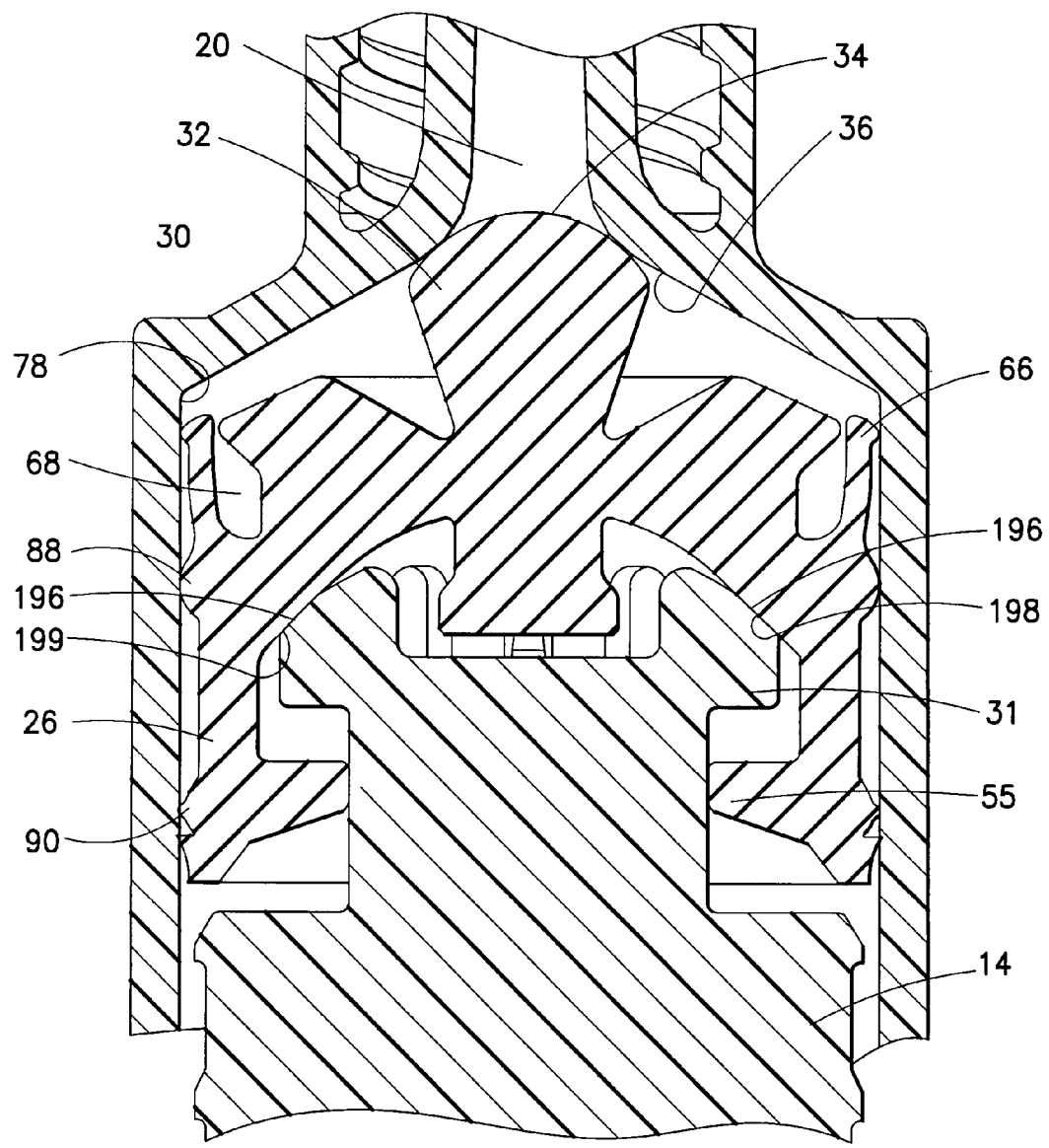
FIG. 13 is a cross-sectional side view of a stopper/plunger arrangement utilizing the stopper embodiment of FIG. 6C during a first reflux reduction step of the invention.
Figure 14:
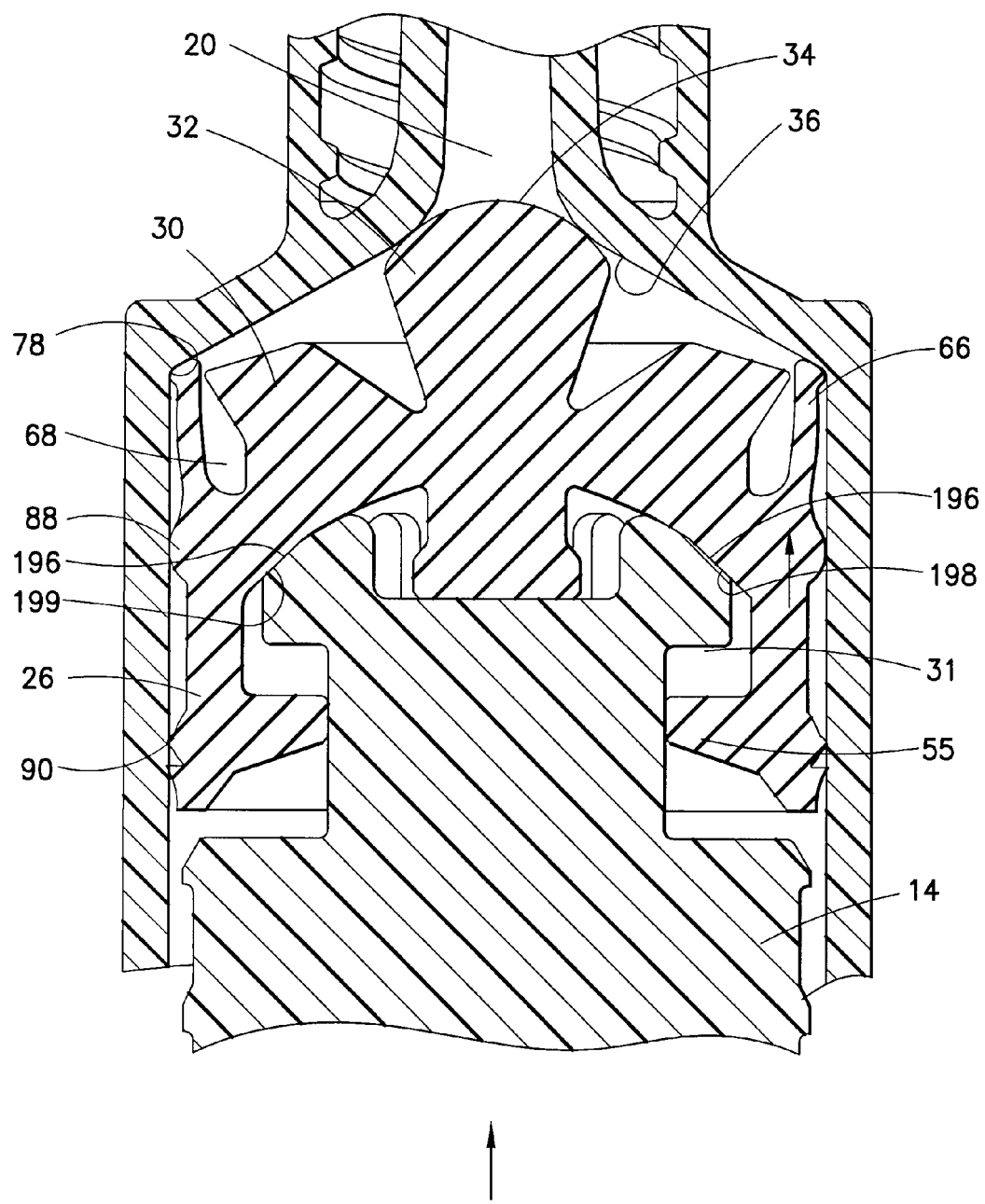
FIG. 14 is a cross-sectional side view of a stopper/plunger arrangement utilizing the stopper embodiment of FIG. 6C during a second reflux reduction step of the invention.
Figure 15:
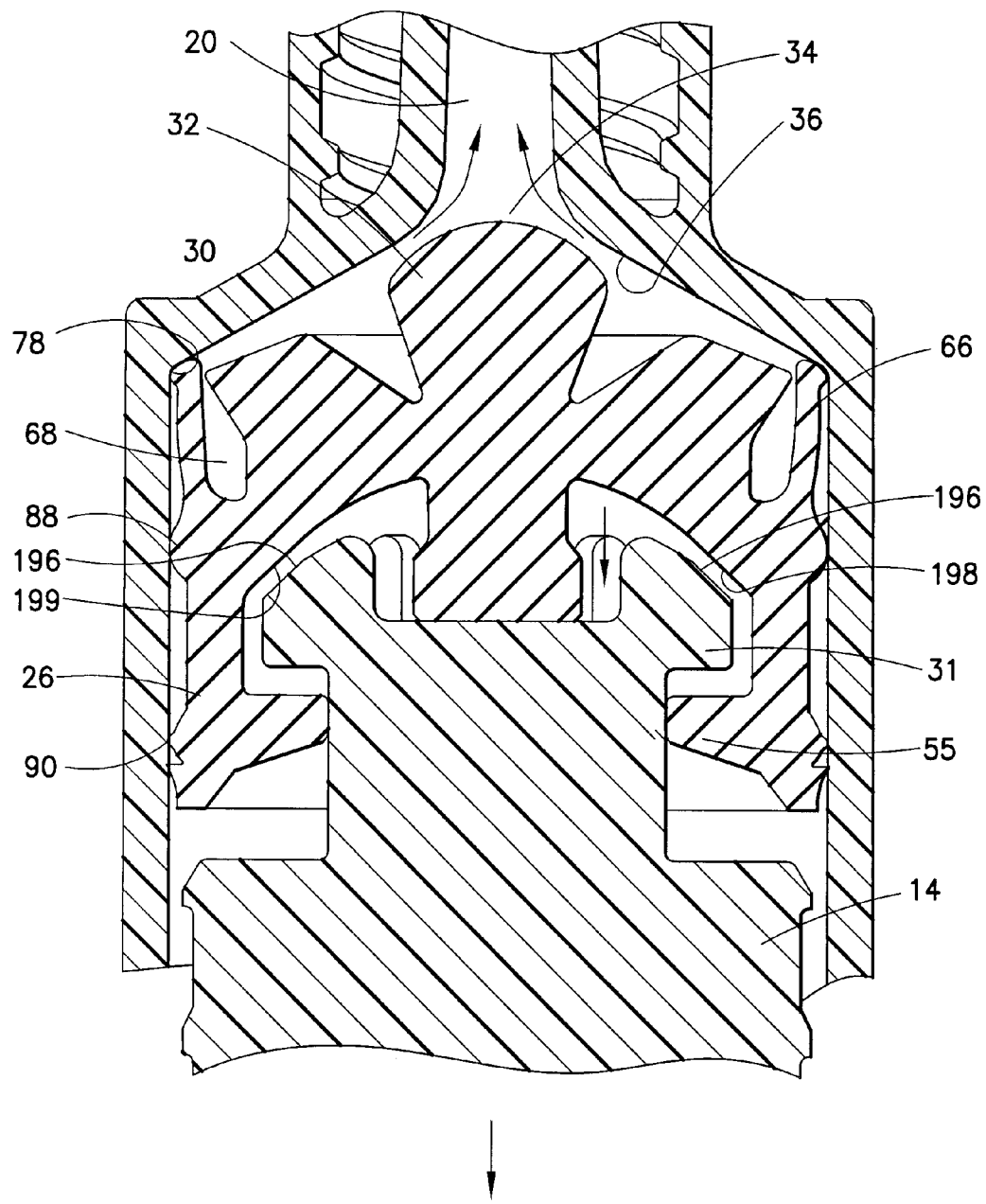
FIG. 15 is a cross-sectional side view of a stopper/plunger arrangement utilizing the stopper embodiment of FIG. 6C during a third reflux reduction step of the invention.

A method of positively displacing fluid and preventing reflux within a syringe barrel utilizing the stopper design of FIG. 6C is also provided by the present invention and is illustrated in FIGS. 13-15. This method comprises the steps of providing a stopper 12 comprising a main body 26 having a closed front end 30. The main body 26 may also include an open rearward end 28 which is adapted to receive a front forward end attachment member 31 of a plunger rod 14 therein. The main body 26 includes a first body portion 60 having a first diameter and a second body portion 62 having a second diameter which is larger than the first diameter of the first body portion 60. A flexible core member 32 is integrally formed with the main body 26 adjacent the closed front end 30. The flexible core member 32 includes a nose portion 34 extending from the front end, a shoulder 64 extending around the first body portion 60 of the main body 26, and at least one perimetrical skirt 66 extending from the second body portion 62 toward the front end 30 of the main body 26. The perimetrical skirt 66 cooperates with the shoulder 64 for trapping at least one air pocket/bubble 68 therein. The perimetrical skirt 66 includes a radially extending bump or first rib 77 along an outer surface lip portion 74. The method further comprises the steps of providing at least a second rib 88 extending radially outward around a perimeter of an outer diameter portion or second body portion 62 of the main body 26, inserting the front forward end attachment member 31 of a plunger rod 14 within the open rearward end 28 of the stopper 12, applying a force to the plunger rod 14 to advance the stopper 12 into the syringe barrel 16 until the nose portion 34 of the flexible core member 32 contacts the back or interior surface 36 of an outlet opening, such as a luer 20, forming a seal and trapping fluid from flowing into the luer 20, applying additional force to the plunger rod 14 to compress the nose portion 34, advancing the second rib 48 within the syringe barrel 16 and compressing the trapped air to form increased pressure within the air pocket 68. Upon completion of the flushing operation, the method includes the step of releasing the force on the plunger rod 14 to release the seal between the nose portion 34 and the interior surface 36 of the luer 20 wherein friction force maintains the second rib 48 in an advanced position within the syringe barrel 12 such that the increased pressure within the air pocket 68 causes any trapped fluid to be pushed through the luer 20 and any attached catheter. When the seal is lost, the pressure and stored energy in the air pocket/bubble 68 is released. This air pocket/bubble 68 will expand forcing fluid out from in the front of the stopper 12. This release of pressure pushes outward through the luer 20 causing fluid to be pushed out through any attached catheter.

The nose portion 34 of the flexible core member 32 has a profile adapted to create a positive seal with the interior surface of the luer 20 of the syringe barrel 16. This core member 32 is interconnected with the main body 26 via a flexible and/or elastic membrane 44. The step of applying additional force to the plunger rod 14 to compress the nose portion 34 causes the flexible membrane 44 to stretch and the step of releasing the force on the plunger rod 14 releases this force on the flexible membrane 44 to cause any trapped fluid to be pushed through the luer 20 and any attached catheter preventing reflux within the syringe barrel 16.

The present invention has numerous advantages over existing plunger rod and stopper designs. In one aspect of the invention, reduced break-loose forces are present when the stopper 12 is first advanced which increases the ease of use of the device and reduce the release that occurs when the stopper 12 is first broken loose. The present designs also improve or reduce the sustaining forces on the stopper 12 due to reduced interference between the stopper 12 and the syringe barrel 16 due to the active seal, which allows the plunger rod 14 and stopper 12 assembly to be used in a wider variety of syringe pump applications. Still another advantage of the inventive assembly is the improved connection between the plunger rod 14 and the stopper 12, especially when the stopper 12 is inserted into the syringe barrel 16 before the plunger rod 14 is attached to the stopper 12. Previous designs, which used a threaded connection, tended to deform the stopper or push it off center, increasing the chance of leakage. Finally, the inventive design achieves a positive displacement of the fluid after the plunger rod 14 is bottomed and the force on the plunger rod 14 is released.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

The invention claimed is:

1. A method of positively displacing fluid from and preventing reflux within a syringe barrel, said method comprising the steps of:
   (a) providing a stopper comprising a main body having a closed front end, a first body portion having a first diameter, a second body portion having a second diameter which is larger than said first diameter, and a core member integrally formed with said main body adjacent said closed front end, said core member including a nose portion, said stopper further comprising a shoulder extending around a perimeter of said first body portion of said main body, and a skirt extending about said first body portion of said main body, said skirt cooperating with said shoulder for trapping at least one air pocket therein;
   (b) advancing the stopper through the syringe barrel until the nose portion of the core member contacts an outlet opening at the forward end of the syringe barrel;
   (c) applying additional force to the stopper to compress the nose portion and increase the pressure within said at least one air pocket; and
   (d) releasing the force on the stopper to release the seal between the nose portion and the outlet opening at the forward end of the syringe while maintaining the main body of the stopper in an advanced position relative to a starting position within the syringe barrel, such that the increased pressure within the at least one air pocket causes any trapped fluid to be expelled through said outlet opening.

2. The method of claim 1, wherein said main body of said stopper includes an open rearward end with a plunger rod inserted within said open rearward end.

3. The method of claim 1, wherein said nose portion of said stopper has a profile adapted to create a positive seal with an interior surface of the outlet opening of the syringe barrel.

4. The method of claim 1, wherein said core member is interconnected with said main body via a flexible membrane enabling the core member to move independently from the main body.

5. The method of claim 4, wherein said step of applying additional force to said stopper to compress said nose portion causes said flexible membrane to stretch and said step of releasing the force releases said flexible membrane to cause any trapped fluid to be expelled through said outlet opening.

6. The method of claim 4, wherein said stopper further includes a first rib on an outer surface of said skirt and at least a second rib extending radially outward around the second portion of said main body, wherein said step of applying additional force to said stopper advances the second rib within the syringe barrel and compresses the trapped air and increases the pressure within said air pockets; and wherein said second rib is maintained in an advanced position relative to the starting position within the syringe barrel when the force on the stopper is released, thereby maintaining the main body of the stopper fixed within the syringe barrel.

7. The method of claim 1, wherein said main body comprises an inner surface having a curved contour from a side wall portion of said main body to said core member, said inner surface adapted for contact with a taper on a front forward end attachment portion of the plunger rod to apply a radial force to the syringe barrel upon the application of a forward force to the plunger rod.

8. A method of preventing reflux within a syringe barrel, said method comprising the steps of:
   (a) providing a stopper comprising a main body defining an open rearward end and a closed front end, said open rearward end adapted to receive a front attachment member of a plunger rod therein, a core member integrally formed with said main body adjacent said closed front end, said core member including a nose portion, said stopper further comprising at least one rib extending radially outward around a perimeter of said main body and wherein said main body includes an inner surface adapted for contact with a taper on a front attachment member of a plunger rod, said inner surface of said main body and said taper cooperating together such that the stopper applies a radial force to the syringe barrel upon the application of a forward force to the plunger rod;
   (b) inserting a front attachment member of a plunger rod within the open rearward end of said stopper;
   (c) applying a force to said plunger rod to advance the stopper into the syringe barrel until the nose portion of the core member contacts an outlet opening at a front end of the syringe barrel forming a seal and trapping fluid from flowing out into the outlet opening;
   (d) applying additional force to said plunger rod to compress at least a portion of said stopper, so as to advance the at least one rib within the syringe barrel and to compress the trapped fluid to form increased pressure;
   (e) releasing the force on said plunger rod to release the seal between the nose portion and the outlet opening of the syringe barrel wherein friction force maintains said at least one rib in an advanced position relative to a starting position within the syringe barrel such that the increased pressure causes any trapped fluid to be pushed through said outlet opening.

9. The method of claim 8, wherein said nose portion has a profile adapted to create a positive seal with an interior surface of the outlet opening of the syringe barrel.

10. The method of claim 8, wherein said core member is interconnected with said main body via a flexible membrane enabling the core member to move independently from the main body.

11. The method of claim 10, wherein said step of applying additional force to said plunger rod to compress said nose portion causes said flexible membrane to stretch and said step of releasing the force on the plunger rod releases this force on the flexible membrane to cause any trapped fluid to be pushed through said outlet opening.

12. The method of claim 8, wherein said stopper includes at least one forward extending skirt extending from a front end of said main body and wherein said step of applying a force to advance the stopper into the syringe barrel causes said skirt to deflect inward with respect to the stopper main body and to contact the stopper main body, thereby trapping fluid within a space between said skirt and said main body.

13. The method of claim 12, wherein the main body further includes a shoulder extending around a perimeter of the main body, such that the skirt extends inwardly and contacts the shoulder, thereby establishing the space between the skirt and the main body.

14. The method of claim 8, wherein said main body comprises an inner surface having a curved contour from a side wall portion of said main body to said core member, said inner surface adapted for contact with the taper on the front attachment member of the plunger rod to apply a radial force to the syringe barrel upon the application of a forward force to the plunger rod.

* * * * *